United States Patent
Fujieda

[11] Patent Number: 5,907,388
[45] Date of Patent: May 25, 1999

[54] OPHTHALMIC MEASUREMENT APPARATUS HAVING PLURAL PAIRS OF PHOTORECEIVING ELEMENTS

[75] Inventor: Masanao Fujieda, Toyohashi, Japan

[73] Assignee: Nidek Co., LTD., Gamagori, Japan

[21] Appl. No.: 08/942,633

[22] Filed: Oct. 2, 1997

[30] Foreign Application Priority Data

Oct. 3, 1996 [JP] Japan .................................. 8-283280
Oct. 3, 1996 [JP] Japan .................................. 8-283281

[51] Int. Cl.$^6$ .......................................................... A61B 3/10
[52] U.S. Cl. ............................................ 351/211; 351/221
[58] Field of Search ................................... 351/211, 221, 351/212, 205, 206, 246, 247, 200

[56] References Cited

U.S. PATENT DOCUMENTS

| | | |
|---|---|---|
| 4,390,255 | 6/1983 | Nohda et al. . |
| 4,526,451 | 7/1985 | Nohda . |
| 4,702,596 | 10/1987 | Nohda . |
| 4,787,743 | 11/1988 | Nohda . |
| 4,917,458 | 4/1990 | Matsumura . |
| 5,214,456 | 5/1993 | Gersten . |
| 5,500,697 | 3/1996 | Fujieda . |
| 5,555,039 | 9/1996 | Iki et al. . |

FOREIGN PATENT DOCUMENTS

| | | |
|---|---|---|
| A1 0 210 722 | 2/1987 | European Pat. Off. . |
| 29 51 897 | 7/1980 | Germany . |
| B2-61-11090 | 4/1986 | Japan . |
| A-63-46130 | 2/1988 | Japan . |
| A-8-103413 | 4/1996 | Japan . |

*Primary Examiner*—Hung Xuan Dang
*Attorney, Agent, or Firm*—Oliff & Berridge, PLC

[57] ABSTRACT

An ophthalmic measurement apparatus for measuring a refractive power of an eye to be examined, the apparatus comprises slit projecting optical system for scanning a fundus of the eye by a slit light bundle, detecting optical system for detecting the slit light bundle reflected by the fundus of the eye which is scanned by the slit projecting optical system, the detecting optical system includes plural pairs of photo-receiving elements which are disposed along the meridian direction corresponding to the slit scanning direction of the slit light bundle, and respective pairs of photo-receiving elements are disposed so as to be symmetric with putting an optical axis therebetween at approximately conjugate position relative to a cornea of the eye, and refractive power calculating device for calculating the refractive power of the eye which is varied at the meridian direction, based on respective phase difference signals outputted by respective photo-receiving elements of the detecting optical system.

19 Claims, 16 Drawing Sheets

PHOTO-RECEIVING
ELEMENT 15a

PHOTO-RECEIVING
ELEMENT 15b

PHOTO-RECEIVING
ELEMENT 15g

PHOTO-RECEIVING
ELEMENT 15h

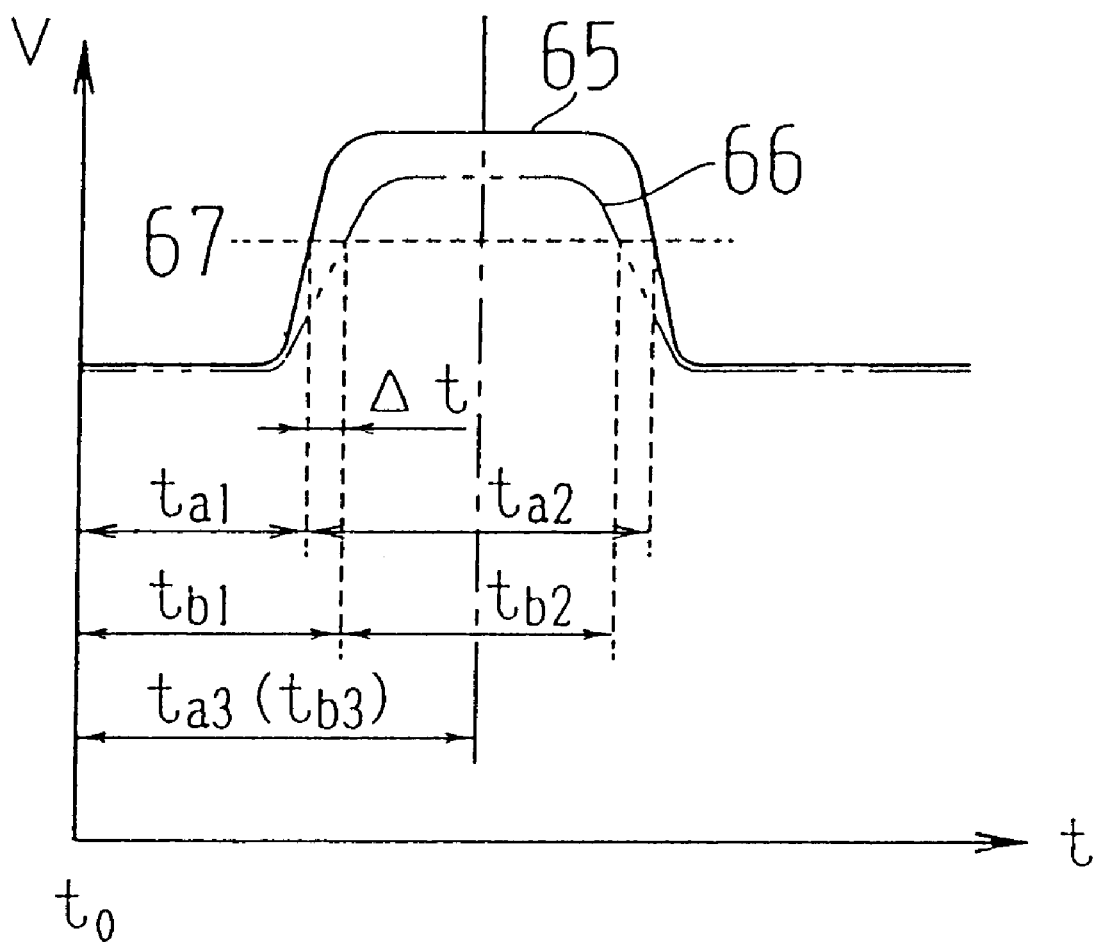

PULSE WAVE FOR MEASUREMENT

PHOTO-RECEIVING ELEMENT 15a

PHOTO-RECEIVING ELEMENT 15b

PHOTO-RECEIVING ELEMENT 15g

PHOTO-RECEIVING ELEMENT 15h

REFRACTIVE POWER
COLOR SCALE

PULSE WAVE FOR
MEASUREMENT

PHOTO-RECEIVING
ELEMENT 15a

PHOTO-RECEIVING
ELEMENT 15b

PHOTO-RECEIVING
ELEMENT 15c

PHOTO-RECEIVING
ELEMENT 15d

ROTATING DIRECTION

OPHTHALMIC MEASUREMENT APPARATUS HAVING PLURAL PAIRS OF PHOTORECEIVING ELEMENTS

BACKGROUND OF THE INVENTION

1. Field of the Invention

The present invention relates to an ophthalmic measurement apparatus, and more particularly relates to an ophthalmic measurement apparatus such as an eye refractive power measurement apparatus for measuring a refractive power of an eye to be examined objectively.

2. Description of Related Art

In the case that the refractive error is corrected by using spectacles or contact lens, a subjective inspection is performed in order to determine a prescribed value thereof. Upon performing the subjective inspection, such method is widely spread that uses measured data which are measured by an eye refractive power measurement apparatus for measuring a refractive power of an eye to be examined objectively. It is known an eye refractive power measurement apparatus that scans slit-shape light bundle and projects it onto a fundus of the eye, and obtains the refractive power of the eye by detecting the light reflected by the fundus of the eye due to the projection of slit light bundles by means of two pairs of photo-receiving elements which are disposed so as to be symmetric with putting an optical axis therebetween at approximately conjugate position relative to a cornea of the eye. The results measured by the apparatus are calculated and outputted by using three parameters S (spherical power), C (astigmatism (cylindrical) power) and A (astigmatism (cylindrical) axial angle), with defining that the refractive power of the eye is symmetric with respect to the corneal center in order to fit to the prescribed value of spectacles or the like.

However, a refractive power of an eye is not always symmetric with respect to the corneal center, and many eyes have irregular astigmatism. In the case of irregular astigmatism such as keratoconus, there is difference between the measured results of S, C and A obtained at the time when the eye looks at the center of the fixation target inside of the apparatus and the measured results of S, C and A obtained at the time when the eye looks at the point except the center of the fixation target. Therefore, measured data of conventional art does not provide sufficient refractive information enough to perform the subjective inspection efficiently.

Also, recently, the keratorefractive surgery which corrects the refractive error by varying the corneal curvature artificially by removing the corneal surface is noticeable, therefore such apparatus is required that confirms the corneal shape in detail at pre-operation and post-operation, and that recognizes the distribution of the refractive power at respective parts of the cornea. The reason for such requirements, the finally purpose of the keratorefractive surgery resides in to make the distribution of the refractive power of the eye be close to emmetropia (or low myopia, low regular astigmatism).

Further, referring to the keratorefractive surgery by using excimer laser beam which is widely known as recent correcting method for refractive error, the corneal curvature is varied by removing the corneal surface, once there exists the axial deviation, the symmetric performance of the cornea is broken. In addition, referring to such an eye to be examined that is not retained symmetric performance of the refractive power as described above, the measured results of S, C and A often tend to be improper. In this case, the inspection performed for spectacles prescription and the like based on the subjective inspection continued thereafter takes much time, therefore the eye is made to be tired, and it often results in making improper prescribed value.

SUMMARY OF THE INVENTION

The present invention has been made in view of the above circumstances and has an object to overcome the above problems and to provide an ophthalmic measurement apparatus, which may know the condition of the refractive power in detail by measuring the distribution of the refractive power of the eye based on obtaining the refractive power at plural parts of one meridian direction of the cornea and the refractive power at respective parts of numerous meridian direction of the cornea.

Also, another object of the present invention is to provide an ophthalmic measurement apparatus, which may measure the distribution of the corneal curvature and the distribution of the refractive power by using one apparatus and find the relationships between the corneal curvature and the refractive power by making the measured data of the distribution of the corneal curvature be corresponding to the measured data of the distribution of the refractive power.

Further, another object of the present invention is to provide an ophthalmic measurement apparatus, which may obtain the refractive power of the eye based on a higher accurate phase difference method, and may find out existence of irregular astigmatism easily.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic measurement apparatus for measuring a refractive power of an eye to be examined of this invention comprises slit projecting optical system for scanning a fundus of the eye by a slit light bundle detecting optical system for detecting the slit light bundle reflected by the fundus of the eye which is scanned by the slit projecting optical system, the detecting optical system includes plural pairs of photo-receiving elements which are disposed along the meridian direction corresponding to the slit scanning direction of the slit light bundle, and respective pairs of photo-receiving elements are disposed so as to be symmetric with putting an optical axis therebetween at approximately conjugate position relative to a cornea of the eye, and refractive power calculating means for calculating the refractive power of the eye which is varied at the meridian direction, based on respective phase difference signals outputted by respective photo-receiving elements of the detecting optical system.

According to the present invention, the eye refractive power of plural cornea parts of the meridian direction and the distribution of the eye refractive power of respective cornea parts, whereby the condition of the refractive power can be found out in detail.

Also, the ophthalmic measurement apparatus of the present invention further comprises target projecting means for projecting the target for use in measuring corneal shape onto the cornea of the eye, and corneal shape measurement means for obtaining the shape of respective areas of the cornea by detecting and processing the target image which is formed by projecting the target onto the cornea by the target projecting means.

According to the present invention, the distribution of the cornea curvature and the distribution of the refractive power are measured by one apparatus, whereby the relationships between the cornea curvature and the eye refractive power can be found by making the measured distribution of the cornea curvature be corresponding to the measured distribution of the refractive power.

Further, another aspect of the present invention resides in that the ophthalmic measurement apparatus for measuring a refractive power of an eye to be examined, the apparatus comprises slit projecting optical system for scanning a fundus of the eye to be examined by at least two directional slit light bundles, detecting optical system for detecting the slit light bundle reflected by the fundus of the eye which is scanned by the slit projecting optical system by means of plural pairs of photo-receiving elements which are disposed so as to be symmetric with putting an optical axis therebetween at approximately conjugate position relative to a cornea of the eye, the plural pairs of photo-receiving elements including at least not less than a pair of first photo-receiving elements which are disposed along the meridian direction corresponding to the first slit scanning direction of the slit light bundle and at least not less than a pair of second photo-receiving elements which are disposed along the meridian direction not corresponding to the first slit scanning direction of the slit light bundle, center sensing means for sensing either a corneal center or a visual axis center based on the phase difference signal between at least a pair of the second photo-detecting elements, and refractive power calculating means for calculating the refractive power at respective parts of the cornea corresponding to respective positions of the photo-receiving elements based on respective phase difference signals between either the corneal center or the visual axis center sensed by the center sensing means and respective photo-receiving elements which are disposed along the meridian direction corresponding to the first slit scanning direction of the slit light bundle.

According to the present invention, the refractive power of the cornea part of the meridian direction with respect to the cornea center can be obtained, therefore the existence of irregular astigmatism can be found easily, thereby the examiner is made to pay attention upon performing an eye inspection for spectacles prescription and the like thereafter.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIG. 4 is a view showing an example of signal waves derived from both elements at the time when opacities of the corneal part corresponding to a photo-receiving element 15b is serious relative to the corneal part corresponding to a photo-receiving element 15a according to the preferred embodiment;

DETAILED DESCRIPTION OF THE PREFERRED EMBODIMENTS

Figure 1:
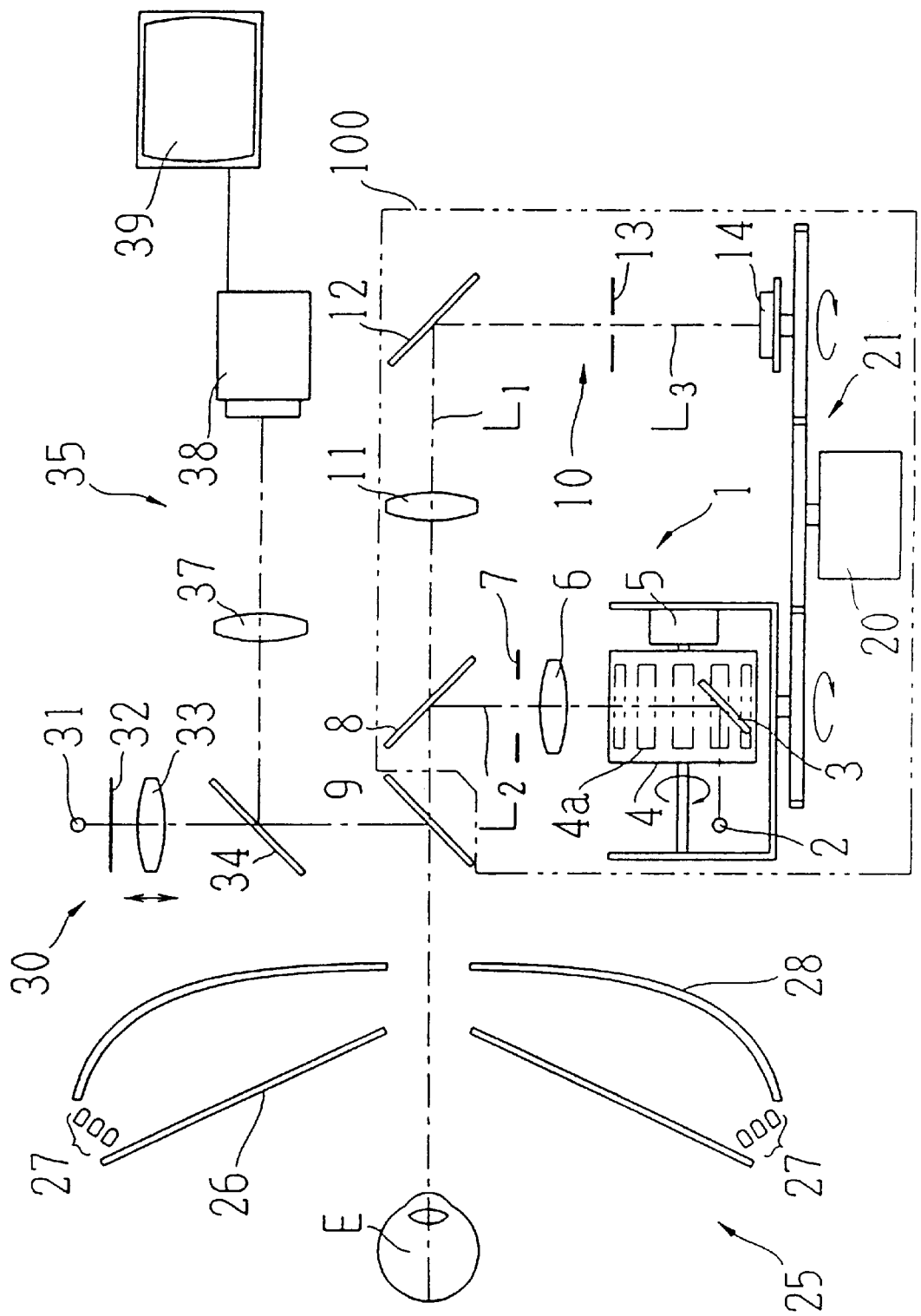
FIG. 1 is a view showing a schematic optical system arrangement of an apparatus according to the first preferred embodiment of the present invention.

A detailed description of one preferred embodiment of an ophthalmic measurement apparatus embodying the present invention will now be given referring to the accompanying drawings. In FIG. 1, there is shown the schematic optical system arrangement of the apparatus according to the preferred embodiment of the first present invention. The optical system consists of an eye refractive power measurement optical system, a fixation target optical system, a target for measuring corneal curvature projecting optical system and a target image for measuring corneal curvature detecting optical system, generally.

Eye Refractive Power Measurement Optical System

An eye refractive power measurement optical system 100 consists of a slit projecting optical system 1 and a slit-image detecting optical system 10. The slit projecting optical system 1 has such construction as following. Numeral 2 denotes a slit illumination light source which emits lights within a range of near infrared rays, and numeral 3 denotes a mirror. Numeral 4 denotes a rotation sector with cylinder shape which is made to be rotated to the fixed direction with fixed velocity by a motor 5. A lot of slit apertures 4a are provided on the side face of the rotation sector 4. Numeral 6 denotes a projecting lens, and the light source 2 is at approximately conjugate position with respect to the projecting lens 6 relative to a position close to an cornea of an eye E to be examined. Numeral 7 denotes a limit diaphragm, and numeral 8 denotes a beam splitter which makes the principal optical axis $L_1$ opposite to the eye E coincide with the optical axis $L_2$ of the slit projecting optical system 1.

The light within a range of near infrared rays which is emitted by the light source 2 is reflected by the mirror 3, and then illuminates the slit aperture 4a of the rotation sector 4. The slit light bundle which is scanned by the rotation of rotation sector 4 passes through the projecting lens 6 and the limit diaphragm 7, and then is reflected by the beam splitter 8. Then, it passes through a beam splitter 9 which makes the optical axis of the fixation target optical system and the optical axis of the observation optical system coincide with the principal optical axis $L_1$, and converges at the position close to the cornea of the eye E, then is projected onto a fundus of the eye E.

Figure 2:
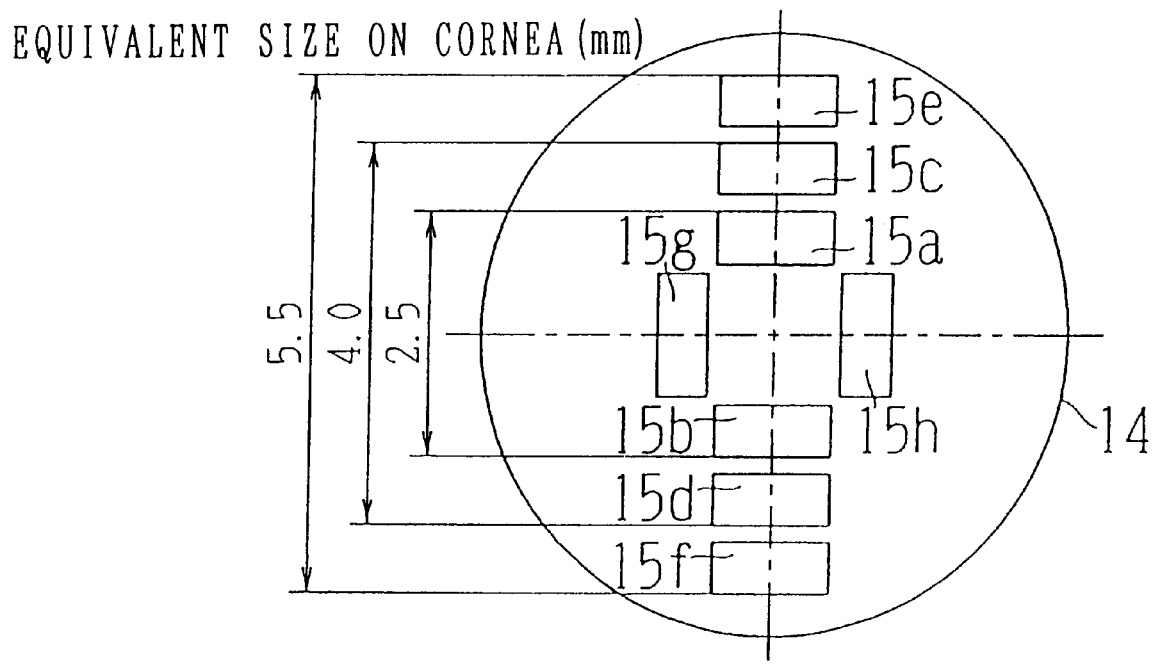
FIG. 2 is a view showing an arrangement of photo-receiving elements provided for the photo-receiving section shown in FIG. 1.

The slit-image detecting optical system 10 includes a receiving lens 11 which is disposed on the principal optical axis $L_1$, a mirror 12, and a diaphragm 13 and a photo-receiving section 14 which are disposed on the optical axis $L_3$ which is reflected by the mirror 12. The diaphragm 13 is disposed at the focusing position of the receiving lens 11 through the mirror 12 (that is, it is at the conjugate position relative to the fundus of the eye E of the emmetropia). The photo-receiving section 14 is provided with the eight photo-receiving elements 15a–15h on the photo-receiving surface thereof as shown in FIG. 2, which are at approximate conjugate position with respect to the receiving lens 11 relative to the cornea of the eye E. The photo-receiving elements 15a–15f except the photo-receiving elements 15g and 15h are on the line which passes through the center of the photo-receiving surface (the optical axis $L_3$), and the photo-receiving elements 15a and 15b, the photo-receiving elements 15c and 15d, and photo-receiving elements 15e and 15f are disposed so as to be symmetric respectively with respect to the center of the photo-receiving surface (that is, with the center at the optical axis $L_3$). The three pairs of photo-receiving elements of which the configuration distance is set so as to detect the refractive power at respective positions of the meridian direction of the cornea (referring to FIG. 2, it is denoted by equivalent size on cornea). On the contrary, the photo-receiving elements 15g and 15h are disposed so as to be symmetric on the line intersecting at 90° relative to the line passing through the photo-receiving elements 15a to 15f with the center at the optical axis $L_3$.

The eye refractive power measurement optical system 100 having such construction of which the slit illumination light source 2 to the motor 5 are constituted so as to rotate with the center at the optical axis $L_2$, and of which the photo-receiving section 14 is constituted so as to rotate with the center at the optical axis $L_3$, being synchronized with each other by means of a rotation mechanism 21 which consists of a motor 20, a gear and the like. And the direction where the photo-receiving elements 15a to 15f on the photo-receiving section 14 are placed is set so as to correspond to the scanning direction (the slit light bundle on the fundus comes to be scanned to the direction intersecting at 90° relative to the long direction of the slit, as it were) of the slit light bundle on the eye E which is projected by the slit projecting optical system 1. Referring to the apparatus of the preferred embodiment, in the case that the slit light bundle by the slit aperture 4a is scanned on the fundus of the eye E having hyperopia or myopia exclusive of astigmatism, the photo-receiving elements 15a to 15f are disposed so as to correspond to the direction intersecting at 90° relative to the long direction of the slit received on the photo-receiving section 14.

Eye Fixation Target Optical System

Numeral 30 denotes an eye fixation target optical system, numeral 31 denotes a visible light source, numeral 32 denotes a fixation target, and numeral 33 denotes a light-throwing lens. The light-throwing lens 33 fogs the eye E by moving to the optical axis direction. Numeral 34 denotes a beam splitter which makes the optical axis of the observation optical system coincide with the optical axis of the eye fixation target optical system 30. The light source 31 illuminates the fixation target 32, the light bundle from the fixation target 32 passes through the light-throwing lens 33 and the beam splitter 34, and then is reflected by the beam splitter 9 to be transmitted to the eye E, the eye E is fixed to the fixation target 32.

Target for Measuring Corneal Curvature Projecting Optical System

A target for measuring corneal curvature projecting optical system 25 has such configuration as following. Numeral 26 denotes a conic placido-plate which is provided with an aperture at the center thereof, of which ring patterns having numerous light passing parts and light intercepting parts are formed on the concentric circle with the center at the optical axis $L_1$. Numeral 27s are plural illumination light sources such as LED or the like, from which the illumination light emitted is reflected by a reflecting plate 28 in order to illuminate the placido-plate 26 approximately uniformly from behind. The light bundle having ring patterns which is passed through the light passing parts of the placido-plate 26 is projected onto the cornea of the eye E.

Target Image for Measuring Corneal Curvature Detecting Optical System

Numeral 35 denotes a target image for measuring corneal curvature detecting optical system. The light bundle reflected by cornea having ring patterns which is projected by the target for measuring corneal curvature projecting optical system 25 is reflected by the beam splitter 9 and the beam splitter 34, and then forms the reflected image of cornea having ring patterns on the photographing element of CCD camera 38. Also, the target image for measuring corneal curvature detecting optical system also serves as an observation optical system, the image of the anterior part of the eye E which is illuminated by the anterior part illumination light source which is not shown is passed through the beam splitter 9, the beam splitter 34 and a photographing lens 37, and then is formed on the photographing elements of the CCD camera 38 to be displayed on TV monitor 39.

Next, the measuring method for the eye refractive power of the present invention will be described hereinafter. The measurement of the eye refractive power of the present invention, firstly, the corneal center (or the visual axis center which means a point of visual axis on the cornea) of the meridian direction where the photo-receiving elements 15a to 15f are placed is determined based on the signals outputted by the photo-receiving elements 15g and 15h, then the refractive power at respective parts of the cornea corresponding to respective photo-receiving elements 15a to 15f with respect to the center are measured. To make the description easier, it will be described making the point of the pair of photo-receiving elements 15a and 15b which are the closest to the optical axis.

It is defined that the slit light bundle by the slit projecting optical system is scanned by the fixed velocity, and also defined that the output signal waves, which are outputted at the time when the slit images reflected by the fundus traverse respective photo-receiving elements 15a, 15b, 15g and 15h, are as shown in FIGS. 3A to 3D. This is the case that the eye E has hyperopia or myopia, and also has astigmatism.

Figure 3A:
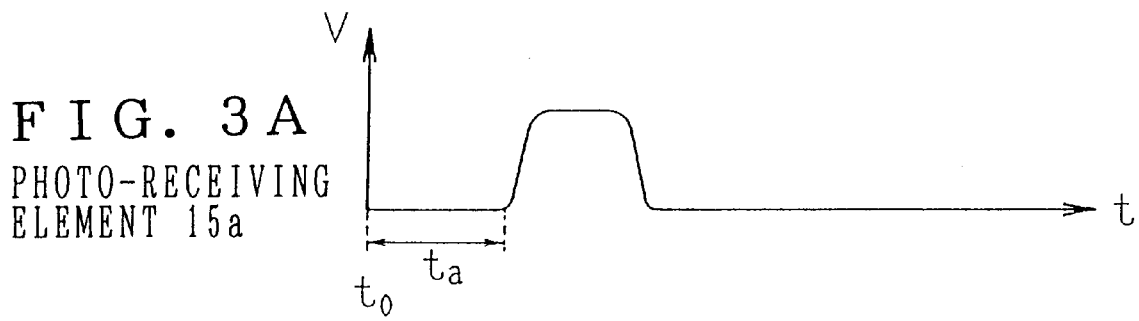
FIGS. 3A to 3D are views showing examples of output signal waves derived from four photo-receiving elements 15a, 15b, 15g and 15h according to the preferred embodiment.
Figure 3B:
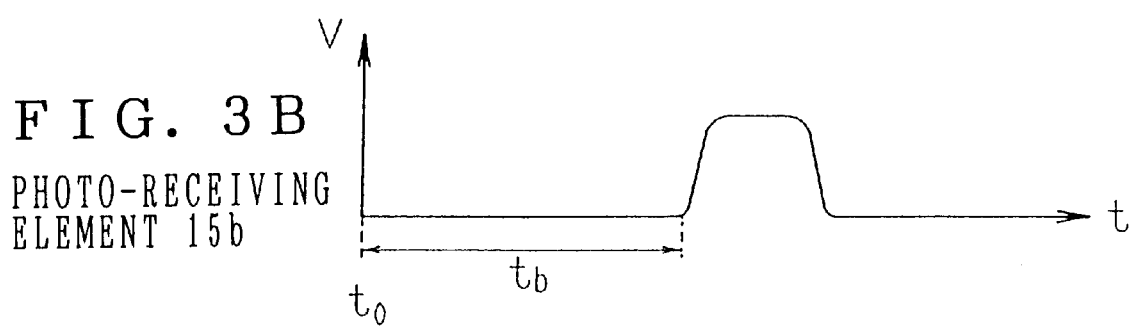
Figure 3C:
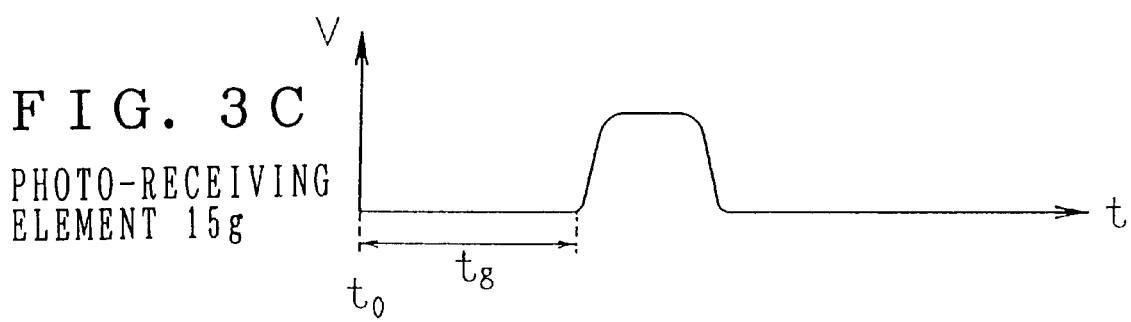
Figure 3D:
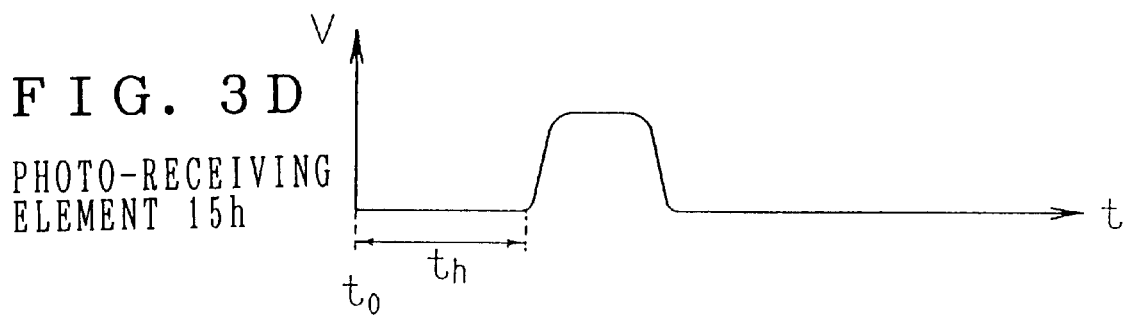

Now, referring to the measurement of the eye refractive power by using the phase difference method, in the case that the refractive power is defined as to be symmetric with respect to the corneal center, the refractive power between the photo-receiving elements 15a and 15b can be obtained by corresponding to the phase difference (the time difference) between the wave signal from the photo-receiving element 15a shown in FIG. 3A and the wave signal from the photo-receiving element 15b shown in FIG. 3B. However, the refractive power is not always symmetric with respect to the corneal center (or the visual axis center). Therefore, firstly, the method for obtaining the center between the photo-receiving elements 15a and 15b based on the photo-voltage signals of the photo-receiving elements 15g and 15h which are positioned in the direction intersecting at 90° relative to the photo-receiving elements 15a and 15b is used. Once the center is determined, the refractive power of corneal part corresponding to the photo-receiving element 15a or 15b can be measured by obtaining the time difference between the corneal part corresponding to the photo-receiving element 15a or 15b and the corneal center (the visual axis center).

Where, to make the description easier, it is defined that respective rising times of photo-voltage signal waves which are generated at respective photo-receiving elements in response to the light incidence is measured ($t_a$, $t_b$, $t_g$ and $t_h$ shown in FIGS. 3A to 3D), then the center between the photo-receiving elements 15a and 15b relative to the time base is given by the expression ($t_g+t_h$)/2. Therefore, if the time difference from the corneal part corresponding to the photo-receiving element 15a to the corneal center is defined as $T_a$, and the time difference from the corneal center to the corneal part corresponding to the photo-receiving element 15b is defined as $T_b$, then the following expressions are given:

$$T_a=[(t_g+t_h)/2-t_a],$$

$$T_b=[t_b-(t_g+t_h)/2],$$

then, the refractive power at corneal part corresponding to the photo-receiving element 15a is measured by calculating the time difference $T_a$, and the refractive power at corneal part corresponding to the photo-receiving element 15b is measured by calculating the time difference $T_b$.

Next, the method for measuring the phase difference time by processing the output signals from respective photo-receiving elements by means of binary-converting processing (converting the output signals into a binary form) will be described hereinafter. In the case that binary-converting processing is performed by setting a threshold level relative to signals outputted by respective photo-receiving elements, if there is the light intensity difference between respective photo-receiving elements, then detection of the phase difference time involves error in some case. It tends to occur in the case that opacities such as cataract exist in the optic media. For example, FIG. 4 is a view showing the signal waves derived from both photo-receiving elements 15a and 15b at the time when opacities of the corneal part corresponding to the photo-receiving element 15b relative to the corneal part corresponding to the photo-receiving element 15a are serious (to make the description easier, the timing of photo-receiving is made to be even). The wave 65 denotes the signal wave from the photo-receiving element 15a, and the wave 66 denotes the signal wave from the photo-receiving element 15b. The wave amplitude of the photo-receiving element 15b is small due to opacities. These analog waves are reformed to be pulse waves with a threshold level 67 by binary-converting processing, then respective rising times $t_{a1}$ and $t_{b1}$ from the time base to have the time difference $\Delta t$ upon being reformed to be the pulse waves. Therefore, in the case that there is the light intensity difference between respective photo-receiving elements, the time difference $\Delta t$ results in to be an error upon converting to the refractive power.

Therefore, in considering the case that there is the light intensity difference between respective photo-receiving elements, the center of the meridian direction to be measured (the corneal center or the visual axis center) and the refractive power relative to the center are obtained by adopting the time from the time base to the half of the pulse-width of respective pulse waves which are reformed. Whereby the influence due to difference of amplitude between respective photo-receiving elements is excluded. That is in FIG. 4, it may be allowed to measure the time $t_{a1}$ and $t_{a2}$, the time $t_{b1}$ and $t_{b2}$, then to measure the time $t_{a3}$ or $t_{b3}$ up to the center thereof. Thereby $t_{a3}$ and $t_{b3}$ are given by following expressions respectively:

$$t_{a3}=t_{a1}+t_{a2}/2,$$

$$t_{b3}=t_{b1}+t_{b2}/2,$$

It means that the exact time can be measured even if the threshold levels upon binary-converting processing corresponding to respective photo-receiving elements are different to some extent.

Figure 5A:
FIGS. 5A to 5E are views for illustrating a method for detecting based on a binary-converting procedure according to the present invention.
Figure 5B:
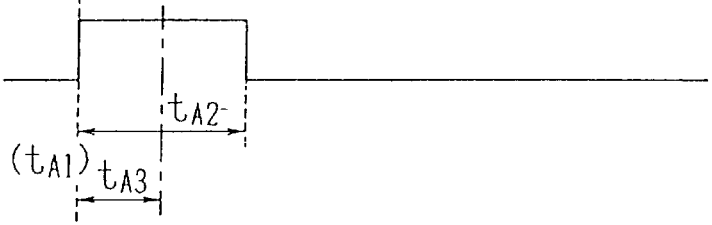
Figure 5C:
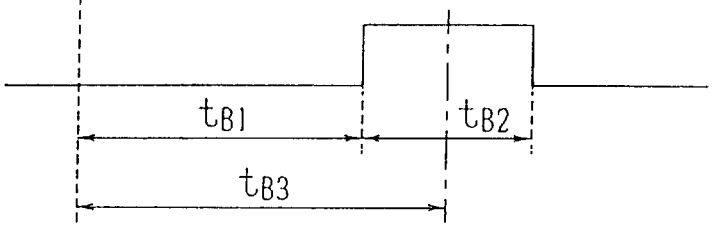
Figure 5D:
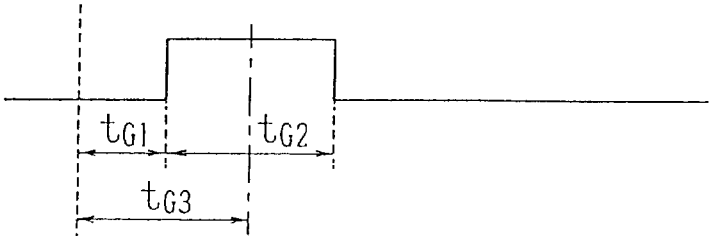
Figure 5E:
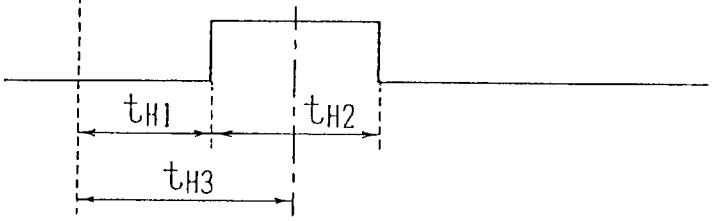

FIGS. 5A to 5E show definitely above method for measuring the time relating to respective photo-receiving elements. FIG. 5A shows the digital wave of the pulse wave for measurement which is used as the standard (measurement duration), in this case, the first rising timing of the pulse wave after the binary-converting processing among the photo-receiving elements 15a, 15b, 15g and 15h is used as the time base for measuring the phase difference time. FIGS. 5B to 5E show the digital waves which are obtained by respective photo-receiving elements, and $t_{A3}$, $t_{B3}$, $t_{G3}$ and $t_{H3}$ denote the time from the time base (rising edge of the pulse wave for measurement) to the center of the pulse width respectively. Therefore, if the direction of the photo-receiving elements 15a and 15b is defined as the meridian direction to be measured, the center thereof (the corneal center) is given by the expression ($t_{G3}+t_{H3}$)/2, then the time difference $T_A$ from the photo-receiving element 15a to the given center and the time difference $T_B$ from the center to the photo-receiving element 15b are given by following expressions:

$$T_A = (t_{G3} + t_{H3})/2 - t_{A3},$$

$$T_B = t_{B3} - (t_{G3} + t_{H3})/2.$$

Whereby the refractive power at corneal part corresponding to the photo-receiving element 15a is measured by calculating the time difference $T_A$, and the refractive power at corneal part corresponding to the photo-receiving element 15b is measured by calculating the time difference $T_B$.

As the same way, the refractive power at the respective parts of the cornea corresponding to respective photo-receiving elements is measured by calculating time differences between the center and the photo-receiving elements 15c, 15d, 15e and 15f. Once the slit projecting optical system 1 and the photo-receiving section 14 are made to rotate 180° around the optical axis with being synchronized, then the refractive power of all meridian direction (360°) can be found.

Also, by measuring the refractive power of the respective parts from the corneal center to the periphery, the refractive power depending on the pupil diameter can be obtained. On the contrary, the pupil diameter of the eye E during measurement can be measured based on whether or not the respective photo-receiving elements of the meridian direction to be measured receive the light reflected by the fundus. In the case of the preferred embodiment, it is measured by the equivalent size on the cornea due to the configuration of the photo-receiving elements 15a to 15f shown in FIG. 2.

Still, referring to the preferred embodiment, three pairs of the photo-receiving elements are disposed, if the photo-receiving elements are disposed more in number, the refractive power at more peripheral part of the eye can be obtained. Also, if the configuration intervals are made to be dense, then the refractive power at more detailed parts can be obtained.

Figure 6:
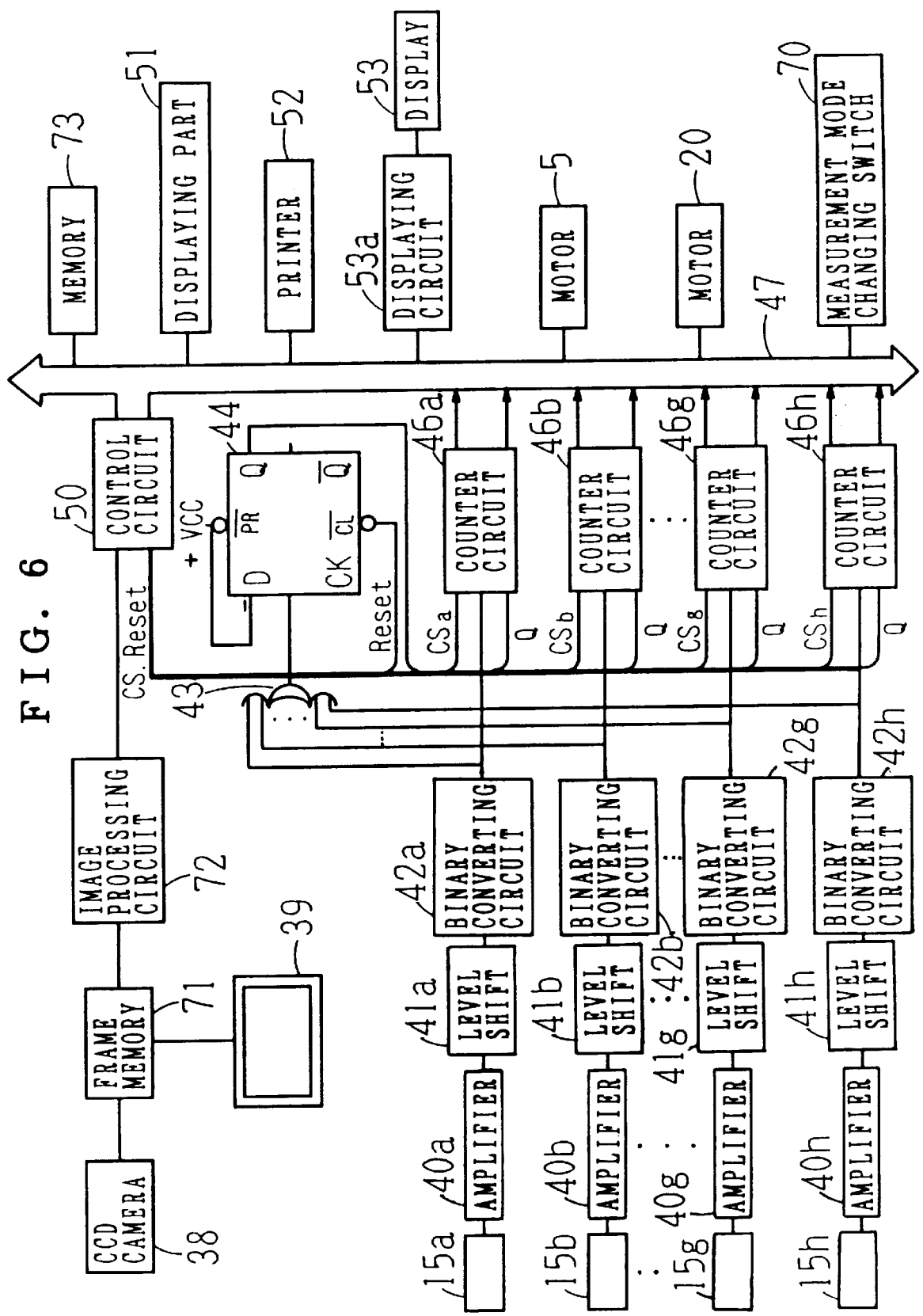
FIG. 6 is a view showing a schematic block diagram of a signal processing system of an apparatus of the first preferred embodiment.

Next, the operation of the apparatus will be described below with reference to the schematic block diagram of the signal processing system shown in FIG. 6. At first, the measurement mode is selected by using measurement mode changing switch 70. The continuous measurement of the corneal curvature measurement and the refractive power measurement will be described.

The examiner moves the apparatus to the vertical and lateral directions and the forward/backward directions while observing the image of the anterior part of the eye E which is illuminated by the illumination light source (not shown) by using the TV monitor 39, thereby the examiner performs the alignment (such known alignment can be used that projects the target for positional adjustment so that the cornea reflecting luminance point and the reticle are made to be the predetermined relationships). Once the alignment is completed, then the measurement is started by generating the trigger signal by using the measurement starting switch not shown.

In the case of the continuous measurement mode, it is started from the corneal curvature measurement. The illumination light source 27 for measuring the corneal curvature is turned on during the predetermined time, and the ring pattern due to the placido-plate 26 is projected onto the cornea. The image of ring pattern which is projected onto the cornea is photographed by the CCD camera 38, and then is stored into a frame memory 71. The image stored into the frame memory 71 is given the edge detecting process by an image processing circuit 72, then the processed data thereof is stored into a memory 73 under a control circuit 50.

Figure 7:
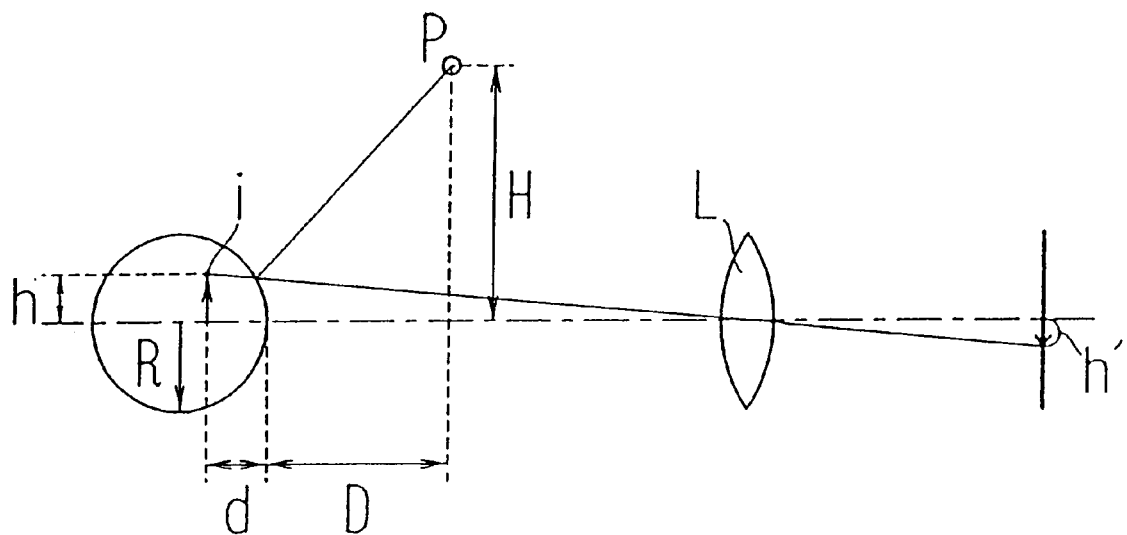
FIG. 7 is a view for illustrating a method for calculating the corneal curvature according to the preferred embodiment.

The control circuit 50 calculates the corneal curvature every predetermined angles based on the detected edge position of the stored data. The calculation for the corneal curvature is as following. As shown in FIG. 7, the detected height is defined as "h'" at the time when the image i due to the corneal convex surface of the light source P at the distance D on the optical axis and the height H from the cornea is formed on the two-dimensional detecting plane by lens L, and the magnification of the optical system of the apparatus is defined as "m", then the corneal curvature radius R is given by following expression (concerning the detail of this calculation, see the Japanese Patent Laid Open No.HEI7(1995)-124113 corresponding to U.S. Pat. No. 5,500,697):

$$R = (2D/H)mh'.$$

Also, the simplified calculating method may be adopted as following. The curvature radius of the area where the j-th ring is projected onto the cornea is defined as $R_j$, the proportional constant which is determined by the height of the j-th ring, the distance up to the eye E and the photographing (image) magnification is defined as $K_j$, and the image height on the photographing plane is defined as $h_j$, the relationship expression as described above is given by $R_j = K_j \cdot h_j$. Where, if plural model eyes having different curvatures which cover the measurement range is measured in advance, then the proportional constant $K_j$ is obtained as a characteristic value of the apparatus, therefore if it is read and utilized for calculating upon measurement, then the distribution of the curvature is obtained in extremely short time. Besides, concerning the calculating processing in the continuous measurement mode, if it is performed after the refractive power measurement has finished, the continuous measurement is performed efficiently.

Continuously, the refractive power measurement is executed. The preliminary measurement of the refractive power is performed by way of the same method as the conventional phase difference method. In the measurement, the light-throwing lens 33 of the eye fixation target optical system 30 is moved based on the refractive power by the preliminary measurement, then the fixation target 32 and the fundus of the eye E are placed at conjugate position, after that, further the adequate quantity of the diopter is made to be fogged. The slit light bundle which is limited by the slit aperture 4a of the slit projecting optical system 1 is passed through the pupil, then is projected onto the fundus. The light bundle which is reflected by the fundus and passed through the pupil is converged by the receiving lens 11 of the slit image detecting optical system 10, then is received by the photo-receiving section 14 through the diaphragm 13. In the case that the eye E is emmetropia, the photo-voltage are generated at the photo-receiving elements 15a to 15h of the photo-receiving section 14 at the same time when the light bundle is transmitted to inside the eye, however, in the case of the refractive error, the light of the slit image which is reflected by the fundus is moved as if it crossed the photo-receiving section 14.

The photo-voltage are generated respectively by photo-receiving elements 15a to 15h (the photo-voltage shows the time difference), based on the movement of the light of the slit image on the photo-receiving section 14. Respective photo-voltage are inputted to respective amplifiers 40a to 40h to which respective photo-receiving elements 15a to 15h are connected, and then amplified, further the shift processing with respect to the respective voltage levels are performed by respective level shift circuits 41a to 41h, then are converted to the pulse signals which are converted to the binary form at the predetermined threshold level by respective binary converting circuits 42a to 42h. Then the respective pulse signals are inputted into respective counter circuits 46a to 46h and OR circuit 43. The OR circuit 43 is used in order to make the first rising edge among respective pulse signals be the rising of the pulse for measurement, then the first rising edge is inputted to a flip-flop 44. The flip-flop 44 gives the pulse signal for measurement which includes the time base (the rising edge) to the respective counter circuits 46a to 46h, and is reset by receiving the Rset signal outputted by the control circuit 50 after all signals is measured.

Once the pulse signals which are converted to binary form by respective binary-converting circuits 42a to 42h, and the pulse signal for measurement from the flip-flop 44 are inputted to respective counter circuits 46a to 46h, then the respective counter circuits 46a to 46h count and hold the rising time and the time of the pulse width of respective pulse signals relative to the rising edge (equivalent to the time base) of the pulse signal for measurement. Referring to FIGS. 5A to 5E as an example, the time from the time base to rising edge of respective pulse are $t_{A1}$ (referring to FIG. 5A, $t_{A1}$=0), $t_{B1}$, $t_{G1}$ and $t_{H1}$, respectively. Also, the time of the pulse width of the digital signals (signals which are converted to binary form) are $t_{A2}$, $t_{B2}$, $t_{G2}$, and $t_{H2}$, respectively.

The time held by respective counter circuits is outputted due to chip-activating signal ($CS_a$ to $CS_h$) generated by the control circuit 50, then inputted to the control circuit 50 through a data bus 47. The control circuit 50 calculates the time of the corneal center of the meridian direction to be measured (the scanning direction of the slit light bundle) by way of above-mentioned method based on the rising time ($t_{A1}$, $t_{B1}$, $t_{G1}$, $t_{H1}$) and the time of the pulse width ($t_{A2}$, $t_{B2}$, $t_{G2}$, $t_{H2}$) of respective pulse signals from respective counter circuits 46a to 46h, then measures the time differences (the phase differences) of three pairs of the photo-receiving elements which are placed in the meridian direction to be measured relative to the center thereof.

Figure 8:
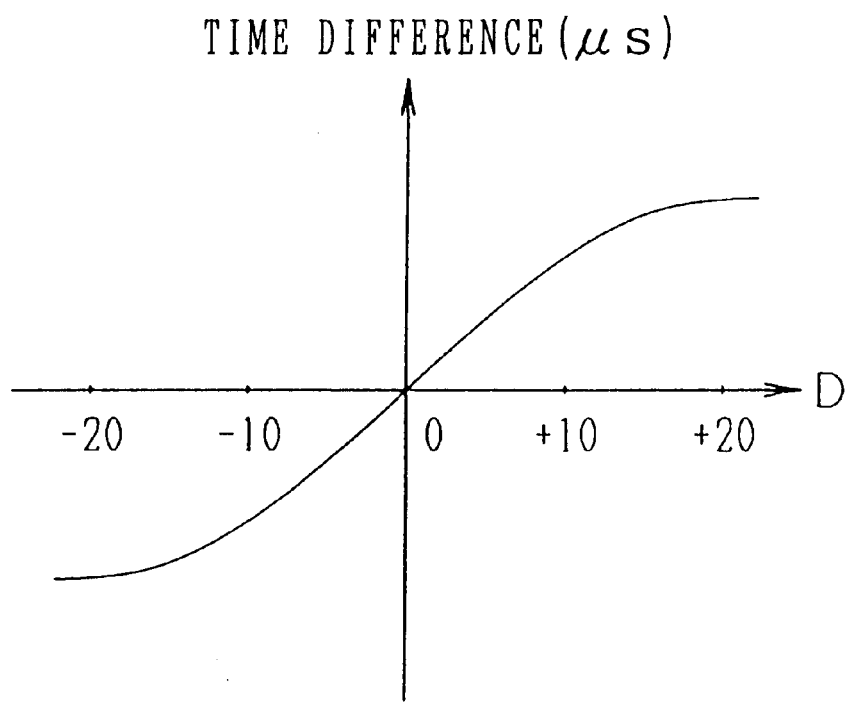
FIG. 8 is a view showing the relationships between the time difference which is detected by the phase-difference method and the refractive power.

Once the time differences at respective corneal parts in one meridian, it is converted into the terms of the refractive power. There is the relationships between time difference which is measured by the phase difference method and the refractive power as shown in FIG. 8. Referring to the relationships, for example, the value of the refractive power corresponding to the time difference is obtained by sampling the data by using the model eye of which the refractive power is known in advance, then by making the data be stored.

Next, the slit illumination light source 2 to the motor 5 of the slit projecting optical system 1 and the photo-receiving section 14 are made to rotate 180° around the optical axis at the predetermined axial intervals (for example, 1°) by driving the motor 20. The refractive power of respective rotation position is obtained based on the signals from respective photo-receiving elements. These refractive power measurement is performed repeatedly, and the results are given the predetermined processing (taking average, the medium value and the like) and stored. Also, the parameters S, C and A which are the same as the conventional art are calculated by giving the predetermined processing to the refractive power in respective meridian directions.

At the same time, the pupil diameter of the eye E during measurement is obtained based on whether respective photo-receiving elements in the measurement meridian direction to be measured receive the light reflected by the fundus or not, therefore if the processing considering its diameter and the distribution of the refractive power is performed, then more profitable information can be provided upon performing the subjective inspection.

Figure 9:
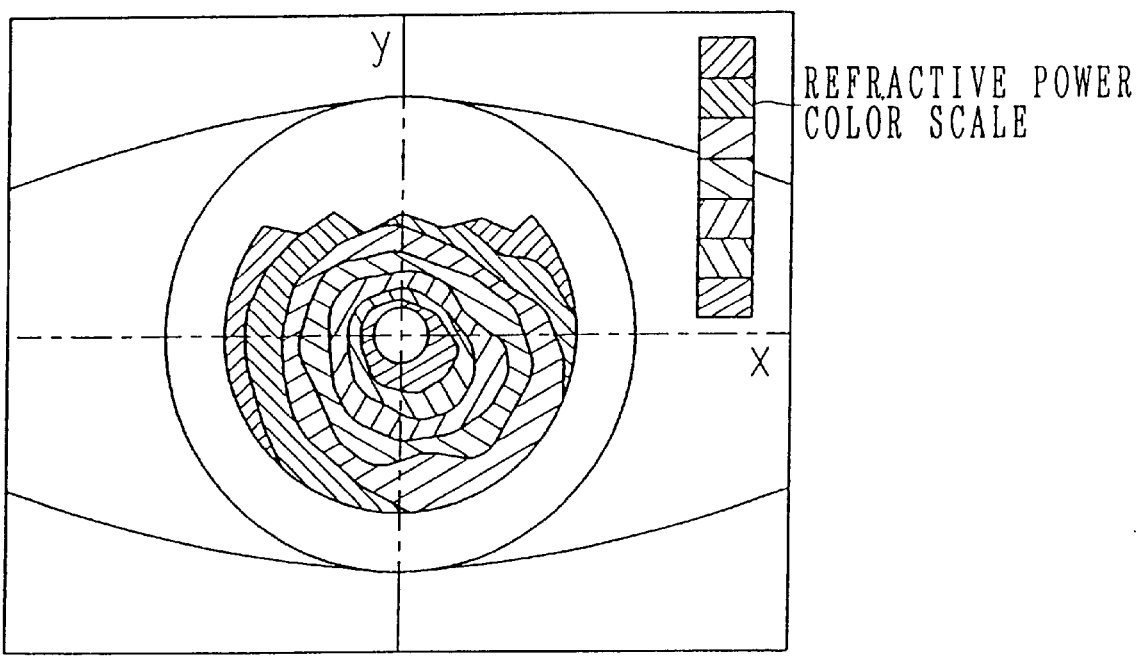
FIG. 9 is a view showing a displaying example of the measurement data of the distribution of the refractive power according to the preferred embodiment.
Figure 10:
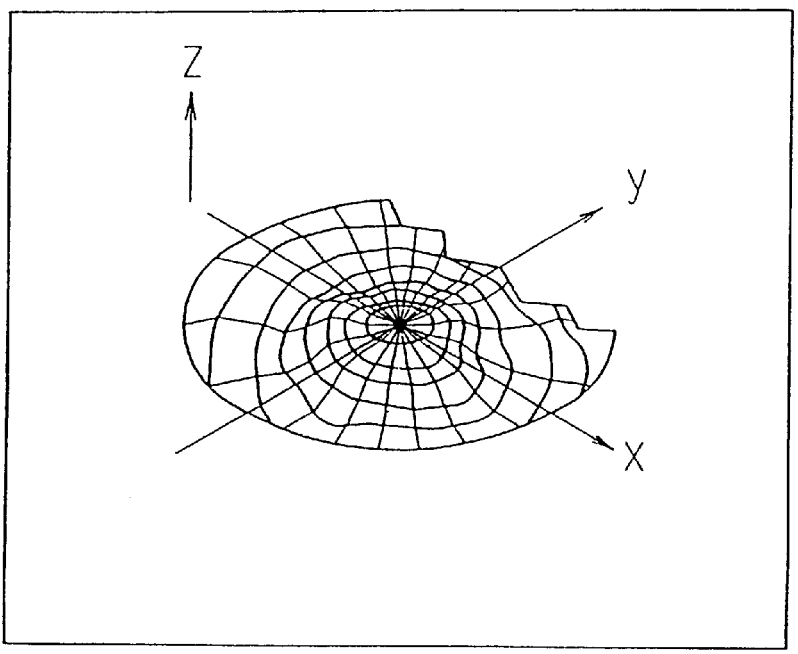
FIG. 10 is a view showing another displaying example of the measurement data of the distribution of the refractive power according to the preferred embodiment.

The measurement data of the distribution of the refractive power obtained as described above are displayed at the display 53 through the displaying circuit 53a. FIG. 9 and FIG. 10 are examples thereof. FIG. 9 is a front view showing the distribution of the refractive power by using a color map (or a gray scale). In the figure, the upper part where the color map broken is the part where the photo-receiving element can not receive the light reflected by the fundus due to the eyelashes, resulting in that the distribution of the refractive power is not obtained. FIG. 10 is an example of the distribution of the refractive power by way of stereoscopic display.

Besides, referring to the preferred embodiments, the refractive power at three parts in the radius direction of the cornea is obtained by the three pairs of the photo-receiving elements, however, the refractive power at more parts in radius direction can be obtained by interpolating the refractive power between the obtained corneal parts, therefore the distribution condition comes to be easier to recognize.

Also, the distribution condition of the curvature radius can be displayed as FIG. 9 and FIG. 10 by converting the curvature radius obtained by the corneal curvature measurement to the refractive power of the cornea by way of known method. Further, if the distribution of the corneal curvature (distribution of the corneal refractive power: D=(n−1)/r, r=corneal curvature, n=equivalent refractive index of cornea) and the distribution of the eye refractive power are displayed at the same time by making them corresponding to each other, the relationships therebetween can be known.

Further, in order to correspond the distribution of the eye refractive power to the distribution of the corneal refractive power, if the cylindrical refractive power component is fetched from the refractive power of the cornea, then the cylindrical refractive power component can be compared with the astigmatism component of the eye refractive power or difference therebetween can be displayed. Thereby, the distribution condition of the residual astigmatism of the eye E (difference between the total astigmatism of the eye E and the corneal astigmatism) can be recognized.

By understanding the refractive condition of the eye E, as is descried above, even if the keratorefractive surgery is performed, the data for treating adequately can be provided.

Also, the pupil diameter of the eye E upon measuring are measured at the same time, the information can be made use of the spectacles prescription and the like in the case of the subjective inspection.

Figure 12:
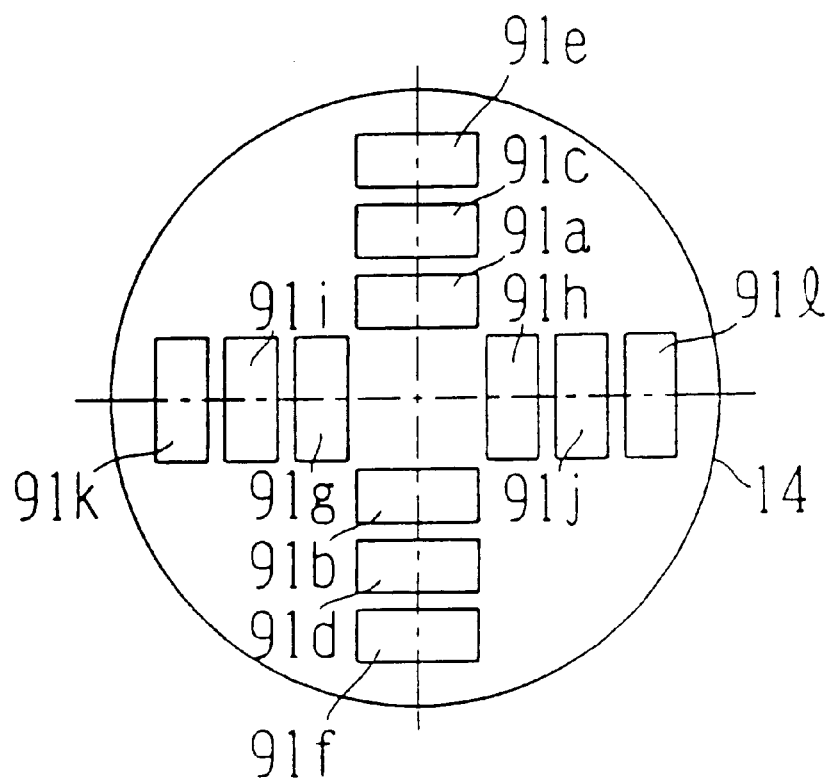
FIG. 12 is a view showing an example of an arrangement of photo-receiving elements in the case that the measurement of two meridian directions shown in FIG. 11 are performed.

The present invention may be embodied in other specific forms without departing from the spirit or essential characteristics thereof. For instance, the rotation sector 4 is provided for a lot of slit apertures 90a and 90b having two kinds of different angle of inclination, respectively. That is, the slit aperture 90a is disposed so as to be at an inclination angle of 45° with respect to the rotation direction of the rotation sector 4, and the slit aperture 90b is disposed so as to be at an inclination angle of 135° with respect to the rotation direction so that the slit aperture 90b may intersect at 90° with respect to the slit aperture 90a. On the contrary, the three pairs of the photo-receiving elements 91a to 91f and the three pairs of the photo-receiving elements 91g to 91l are disposed on the line intersecting at 90° so as to be correspond to the scanning direction of the slit apertures 90a and 90b on the photo-receiving section 14 as shown in FIG. 12. Whereby the refractive power of respective parts of the cornea corresponding to the arrangement of respective photo-receiving elements in the two meridian directions corresponding to the two kinds of the slit scanning directions intersecting at 90° each other are measured. Therefore, if the slit projecting optical system 1 and the photo-receiving section 14 are made to be rotated 90° with synchronizing each other around the optical axis, then the refractive power of all meridian directions are measured, resulting that the measurement time can be shortened compared with the above-mentioned arrangement. Further, if the number of the angle of inclination of the slit light bundle is made to be increased, and in response to this increase, the disposing directions of the photo-receiving elements on the photo-receiving section 14 is made to be increased, then refractive power of more meridian directions can be measured with the rotation angle being made to be small.

Also, in the case that it is not needed that the meridian directions are divided to the numerous directions, such apparatus may be made that obtains the simplified distribution of the refractive power in response to the number of the disposing direction of the photo-receiving elements without providing the rotation mechanism.

Figure 11:
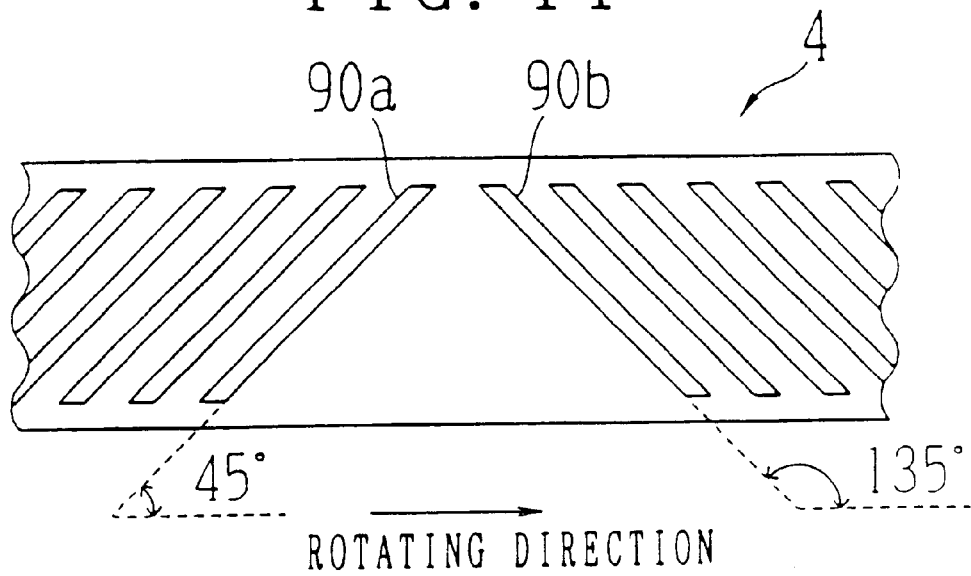
FIG. 11 is a view showing an example of an arrangement of slit apertures in the case that the measurement of two meridian directions are performed, according to the modified example of the preferred embodiment.
Figure 13:
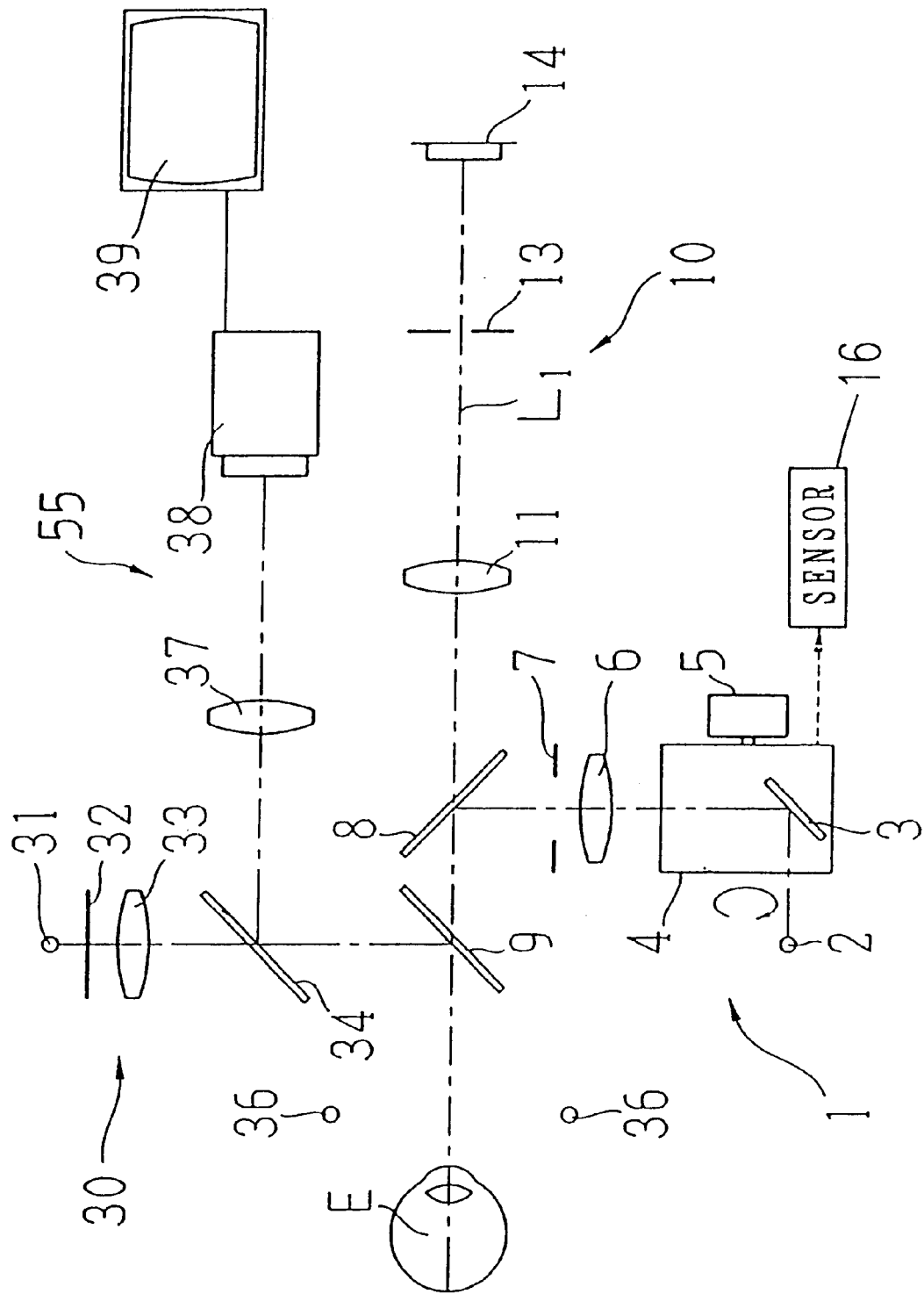
FIG. 13 is a view showing a schematic optical system arrangement of an apparatus according to the second preferred embodiment of the present invention.
Figure 14:
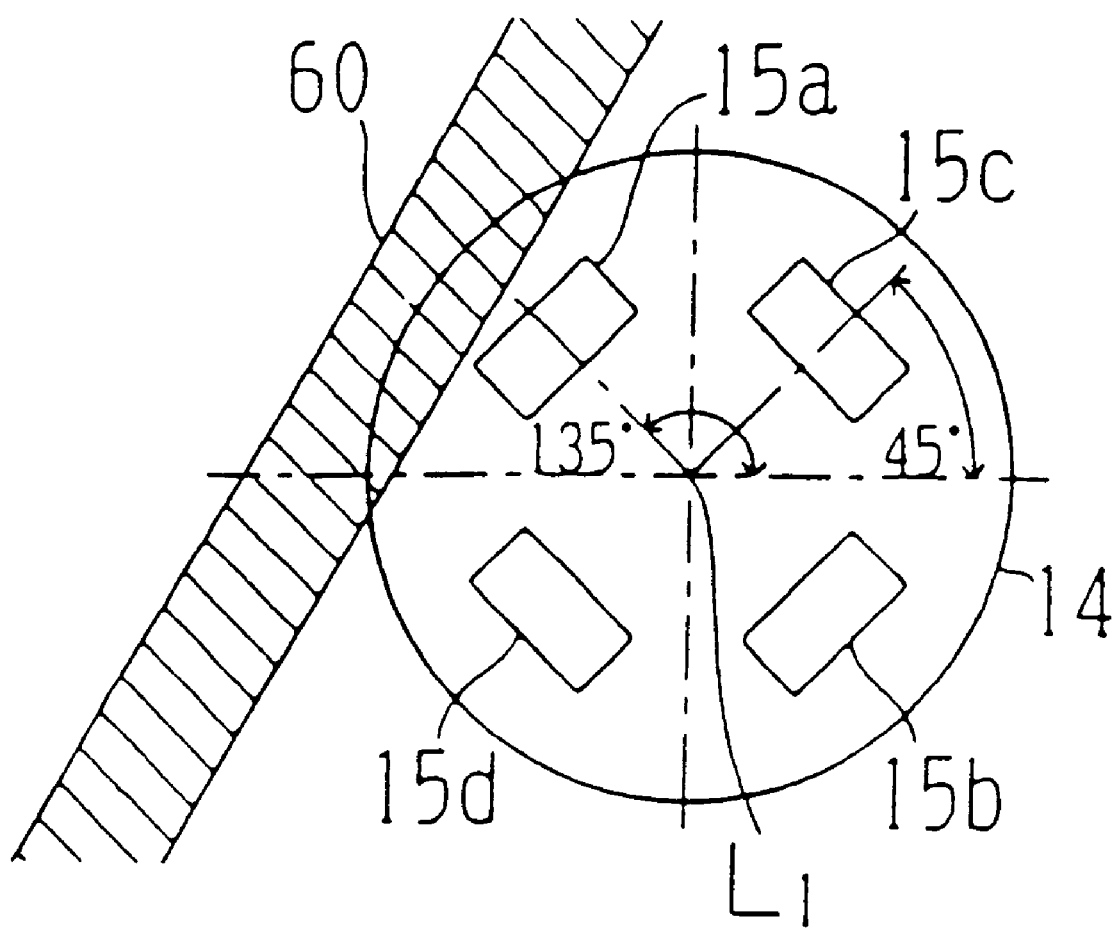
FIG. 14 is a view showing an arrangement of four photo-receiving elements provided for the photo-receiving section shown in FIG. 13.

FIG. 13 is a showing a schematic optical system arrangement of an the preferred embodiment of the second present invention. The optical system consists of the slit projecting optical system, a slit detecting optical system, an eye fixation optical system, and an observation optical system. Referring to the second preferred embodiment, on the side face of the rotation sector 4 which is disposed at the slit projecting optical system, as shown in above-mentioned FIG. 11, a lot of slit apertures 90a and 90b having two kinds of different angles of inclination are provided respectively. That is, the slit aperture 90a is disposed so as to be at an inclination angle of 45° with respect to the rotation direction of the rotation sector 4, and the slit aperture 90b is disposed so as to be at an inclination angle of 135° with respect to rotation direction so that the slit aperture 90b may intersect at 90° with respect to the slit aperture 90a.

Light within a range of near infrared rays which is emitted by the light source 2 is reflected by the mirror 3, and then illuminates the slit aperture 90a or 90b of the rotation sector 4. The slit light bundle which is scanned by the rotation of rotation sector 4 passes through the projecting lens 6 and the limit diaphragm 7, and then is reflected by the beam splitter 8. Then, it passes through a beam splitter 9, and converges at close to the cornea of the eye E, then is projected onto a fundus. Besides, the rotation sector 4 is provided with slit apertures of which the inclination angles are different, therefore the sensor 16 detects which slit light bundle having an angle is projected.

On the contrary, the photo-receiving section 14 which is disposed on the optical axis $L_1$ of the slit detecting optical system 10 is provided with the four photo-receiving elements 15a–15d on the photo-receiving surface thereof. The photo-receiving elements 15a and 15b are disposed so as to be symmetric with respect to the optical axis $L_1$, and as the same way, the photo-receiving elements 15c and 15d are disposed so as to be symmetric with respect to the optical axis $L_1$. The two pairs of photo-receiving elements are disposed respectively with corresponding to the scanning direction of the slit light bundle on the fundus of the eye E which is projected by the slit apertures 90a and 90b having two kinds of inclination angles (the slit light bundle on the fundus comes to be scanned to the direction perpendicular to the long direction of the slit, as it were). Referring to the apparatus of the preferred embodiment, in the case that the slit light bundle is scanned by the slit aperture 90a on the fundus of the eye E having hyperopia or myopia exclusive of astigmatism, the pair of photo-receiving element 15a and 15b are disposed so as to correspond to the direction perpendicular to the long direction of the slit which is received on the photo-receiving section 14, as the same way, in the case that the slit light bundle by the slit aperture 90b is scanned, the pair of photo-receiving element 15c and 15d are disposed so as to correspond to the direction perpendicular to the long direction of the slit which is received on the photo-receiving section 14.

Numeral 55 denotes an observation optical system, and numeral 36 denotes an illumination light source which is disposed in the observation optical system 55. The anterior image of the eye E illuminated by the illumination light source 36 passes through the beam splitters 9 and 34, and forms an image on the photographing elements of the CCD camera 38 by the photographing lens 37, then is displayed on the TV monitor 39. The same configuration as the first preferred embodiment shown in FIG. 1 are attached with the same numerical reference, then the description thereof is omitted.

Next, concerning the second preferred embodiment, the measuring method for determining the corneal center (or the visual center), and then measuring the refractive power of respective parts of the cornea corresponding to respective photo-receiving elements, will be described.

Now, it is defined that the the slit light bundle by the slit aperture 90a is scanned by the fixed velocity and the output signal waves are defined as shown in FIGS. 15A to 15D with respect to a time base to at the time when the slit images 60 reflected by the fundus traverse respective photo-receiving elements 15a to 15d. This is the case that the eye E has hyperopia or myopia, and also has astigmatism.

Figure 15A:
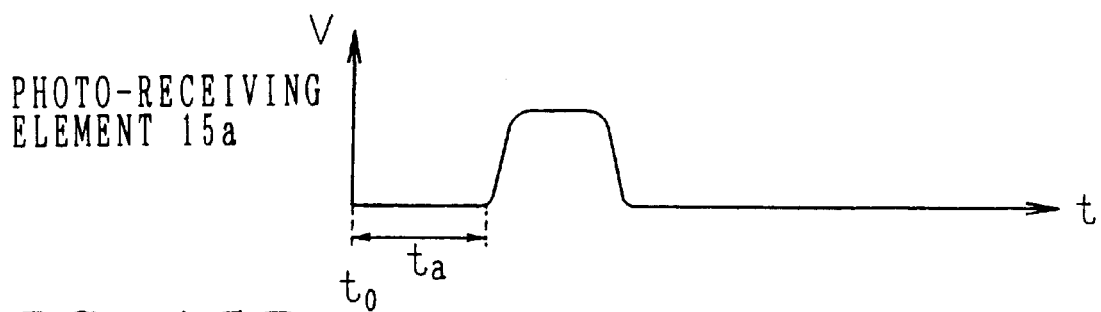
FIGS. 15A to 15D are views showing examples of output signal waves derived from four photo-receiving elements 15a, 15b, 15c and 15d.
Figure 15B:
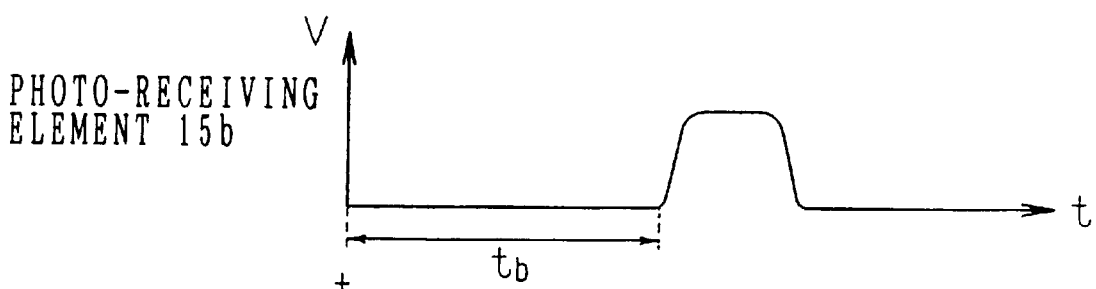
Figure 15C:
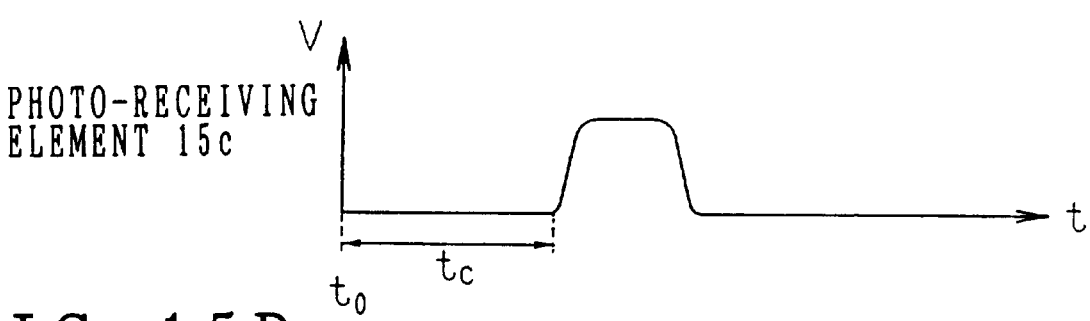
Figure 15D:
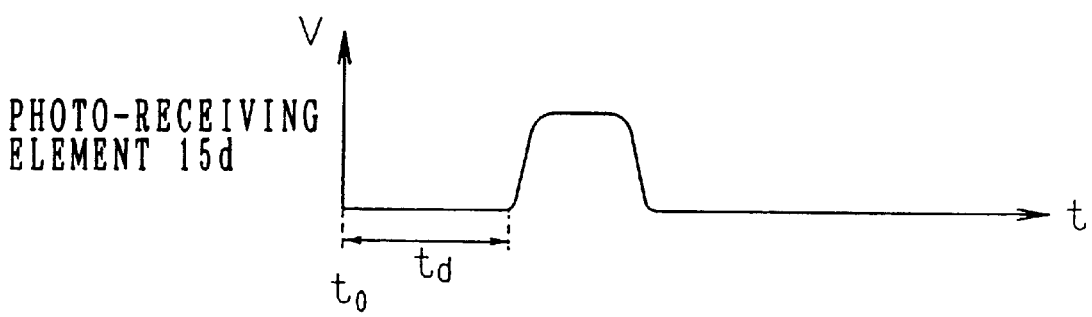

In the case that the refractive power is defined as to be symmetric with respect to the corneal center, the refractive power between the respective parts of the cornea corresponding to respective photo-receiving elements 15a and 15b can be obtained by corresponding to the phase difference (the time difference) between the wave signal from the photo-receiving element 15a shown in FIG. 15A and the wave signal from the photo-receiving element 15b shown in FIG. 15B. However, the refractive power is not always symmetric with respect to the corneal center. Therefore, the method for obtaining the center between the photo-receiving elements 15a and 15b based on the output signals of the photo-receiving elements 15c and 15d which are positioned at the perpendicular direction to the photo-receiving elements 15a and 15b, is used. Then the refractive power at respective parts of the cornea corresponding to respective photo-receiving elements 15a and 15b is measured. Thereby the symmetric performance of the refractive power relative to the center is measured can be estimated.

Where, to make the description easier, it is defined that respective rising times of photo-voltage signal waves which are generated at respective photo-receiving elements in response to the light incidence is measured ($t_a$, $t_b$, $t_c$ and $t_d$ shown in FIGS. 15A to 15D), then the center between the photo-receiving elements 15a and 15b relative to the time base to is given by the expression $(t_c+t_d)/2$. Therefore, if the time difference from the corneal part corresponding to the photo-receiving element 15a to the corneal center is defined as $T_a$, and the time difference from the corneal center to the corneal part corresponding to the photo-receiving element 15b is defined as $T_b$, then the following expressions are given:

$$T_a=[(t_c+t_d)/2-t_a],$$

$$T_b=[t_b-(t_c+t_d)/2],$$

then, the refractive power at corneal part corresponding to the photo-receiving element 15a is measured by calculating the time difference $T_a$, and the refractive power at corneal part corresponding to the photo-receiving element 15b is measured by calculating the time difference $T_b$.

Next, the method for measuring the phase difference time by processing the output signals from respective photo-receiving elements by means of binary-converting processing as has been mentioned in FIG. 4, therefore the description is made simply here, referring to FIG. 4, even if the amplitude of the signal wave 65 from the photo-receiving element 15a is different from the amplitude of the signal wave 66 from the photo-receiving element 15b, once the time $t_{a1}$ and $t_{a2}$, the time $t_{b1}$ and $t_{b2}$ at the time upon reforming to the pulse wave at the threshold level 67 are measured, and then the time $t_{a3}$ or $t_{b3}$ up to the center thereof is measured by using following expressions:

$$t_{a3}=t_{a1}t_{a2}/2,$$

$$t_{b3}=t_{b1}t_{b2}/2,$$

then, even if the threshold levels upon binary-converting processing corresponding to respective photo-receiving elements are different to some extent, the accurate time can be measured.

Figure 16A:
FIGS. 16A to 16E are views for illustrating a method for detecting based on a binary-converting procedure according to the second preferred embodiment of the present invention.
Figure 16B:
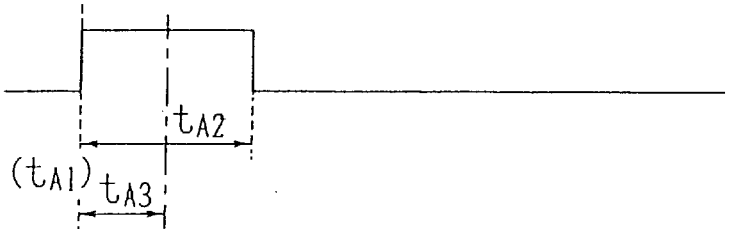
Figure 16C:
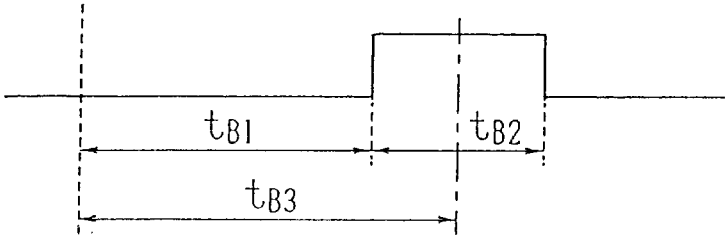
Figure 16D:
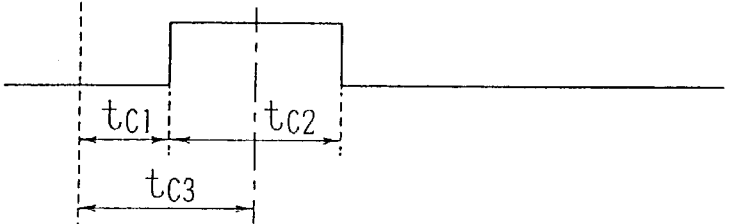
Figure 16E:
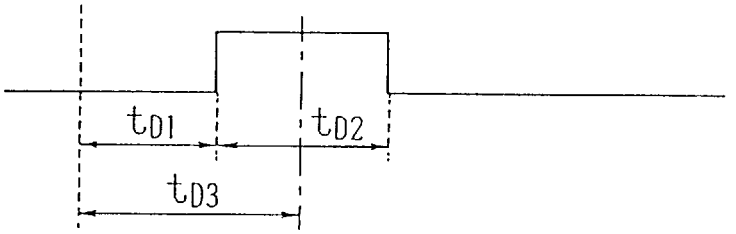

FIGS. 16A to 16E show definitely above method for measuring the time relating to respective photo-receiving elements. FIG. 16A shows the digital wave of the pulse wave for measurement which is used as the standard (measurement duration), in this case, the first rising timing of the pulse wave after the binary-converting processing among the photo-receiving elements 15a to 15d is used as the time base for measuring the phase difference time. FIGS. 16B to 16E show the digital waves which are obtained by respective four photo-receiving elements 15a to 15d, and $t_{A3}$, $t_{B3}$, $t_{C3}$ and $t_{D3}$ denote the time from the time base (rising edge of the pulse wave for measurement) to the center of the pulse width respectively. Therefore, if the direction of the photo-receiving elements 15a and 15b is defined as the meridian direction to be measured, the center thereof (the corneal center) is given by the expression $(t_{C3}+t_{D3})/2$, then the time difference $T_A$ from the photo-receiving element 15a to the given center and the time difference $T_B$ from the center to the photo-receiving element 15b are given by following expressions:

$$T_A=(t_{C3}+t_{D3})/2-t_{A3},$$

$$T_B=t_{B3}-(t_{C3}+t_{D3})/2.$$

Whereby the refractive power at corneal part corresponding to the photo-receiving element 15a is measured by calculating the time difference $T_A$, and the refractive power at corneal part corresponding to the photo-receiving element 15b is measured by calculating the time difference $T_B$.

As the same way, if the direction of the photo-receiving elements 15c and 15d is defined as the meridian direction to be measured, then the center thereof (the corneal center) is determined based on the digital wave from the photo-receiving elements 15a and 15b, and respective time differences at the photo-receiving elements 15c and 15d with respect to the center thereof are also measured.

Figure 17:
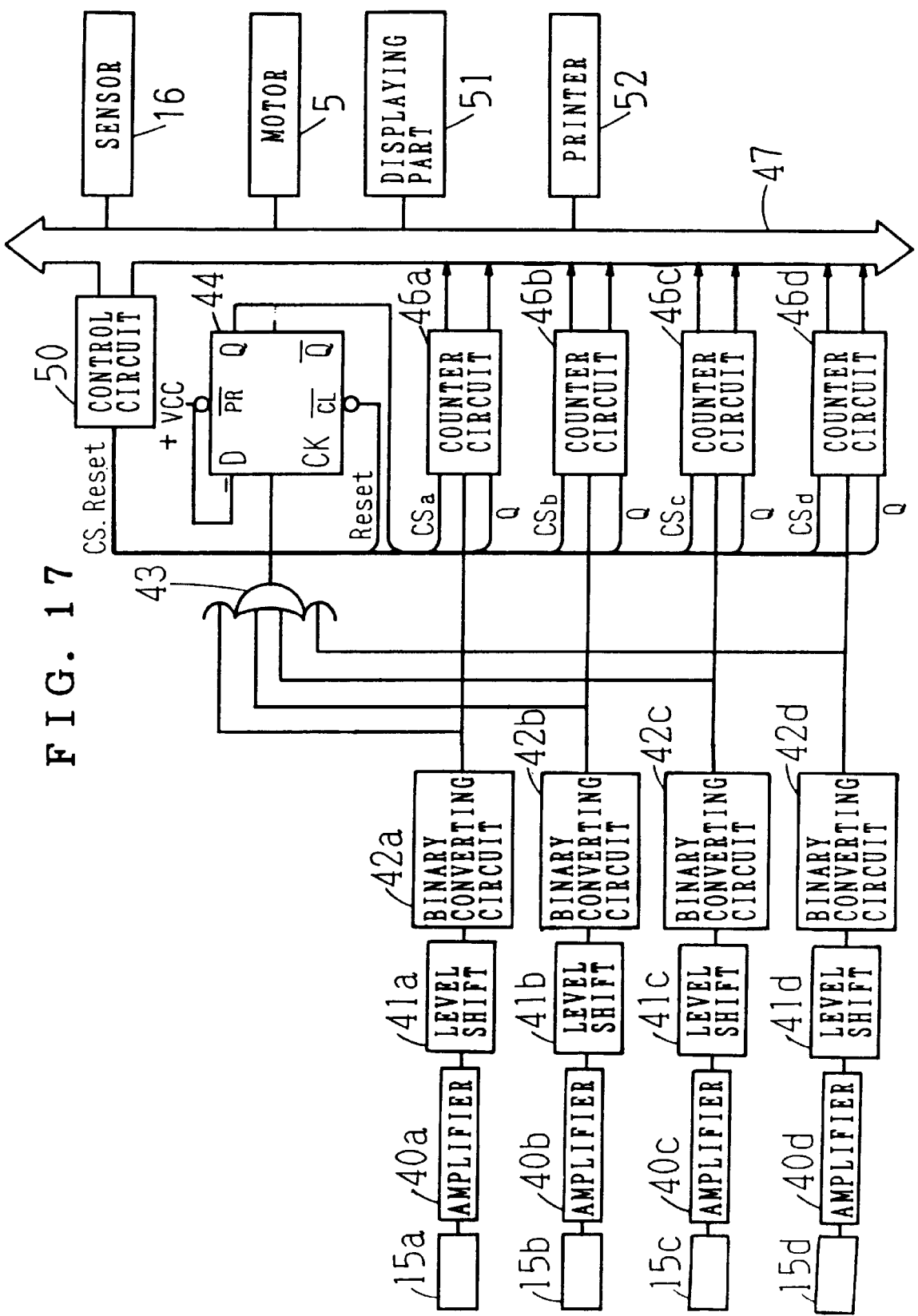
FIG. 17 is a view showing a schematic block diagram of a signal processing system of an apparatus of the second preferred embodiment.

Next, the operation of the apparatus of the second preferred embodiment will be described with referring to the schematic block diagram of the signal processing system shown in FIG. 17. The examiner moves the apparatus to the vertical and lateral directions and the forward/backward directions while observing the image of the anterior part of the eye E which is illuminated by the illumination light source 36 by using the TV monitor 39, thereby the examiner performs the alignment (such known alignment can be used that projects the target for positional adjustment so that the cornea reflecting luminance point and the reticle are made to be the predetermined relationships). Once the alignment is completed, the measurement is started by generating the trigger signal by using the measurement starting switch not shown.

Once the measurement is started, the slit light bundle which is limited by the slit aperture 90a or 90b is passed through the pupil from the slit projecting optical system 1, then is projected onto the fundus under scanning. The light bundle of the slit image which is reflected by the fundus and passed through the pupil is converged by the receiving lens 11 of the slit image detecting optical system 10, then is received by the photo-receiving section 14 through the diaphragm 13. In the case that the eye E is emmetropia, the photo-voltage are generated at the photo-receiving elements 15a to 15d of the photo-receiving section 14 at the same time when the light bundle is transmitted to inside the eye E, however, in the case of the refractive error, the light of the slit image which is reflected by the fundus moves as if it crossed the photo-receiving section 14.

The photo-voltage are generated respectively by photo-receiving elements 15a to 15d (the photo-voltage shows the time difference), based on the movement of the light of the slit image on the photo-receiving section 14. Respective photo-voltage are inputted to respective amplifiers 40a to 40d, and then amplified, further the shift processing with respect to respective voltage levels are performed by respective level shift circuits 41a to 41d, then are converted to the digital signals which are converted to the binary form at the predetermined threshold level by respective binary-converting circuits 42a to 42d. Then the respective pulse signals are inputted into respective counter circuits 46a to 46d and OR circuit 43. The OR circuit 43 is used in order to make the first rising edge among respective pulse signals be the rising of the pulse for measurement, then the first rising edge is inputted to the flip-flop 44. The flip-flop 44 gives the pulse signal for measurement which includes the time base (the rising edge) to the respective counter circuits 46a to 46d, and is reset by receiving the Rset signal outputted by the control circuit 50 after all pulse signals are measured.

Once the pulse signals which are converted to binary form by respective binary-converting circuits 42a to 42d, and the pulse signal for measurement from the flip-flop 44 are inputted respective counter circuits 46a to 46d, then the respective counter circuits 46a to 46d count and hold the rising time and the time of the pulse width of respective pulse signal relative to the rising edge (equivalent to time base) of the measurement pulse signal. Referring to FIGS. 16A to 16E as an example, the time from the time base to the rising edge of respective pulse signals are $t_{A1}$ (referring to FIG. 16A, $t_{A1}=0$), $t_{B1}$, $t_{C1}$ and $t_{D1}$, respectively Also, the time of the pulse width of the digital signals are $t_{A2}$, $t_{B2}$, $t_{C2}$, and $t_{D2}$, respectively.

The time held by respective counter circuits is outputted due to the chip-activating signal ($CS_a$ to $CS_d$) generated by the control circuit 50, then inputted to the control circuit 50 through the data bus 47. The control circuit 50 calculates the time of the corneal center of the meridian direction to be measured (the scanning direction of the slit light bundle) by way of above-mentioned method based on the rising time ($t_{A1}$, $t_{B1}$, $t_{C1}$, $t_{D1}$), the time of the pulse width ($t_{A2}$, $t_{B2}$, $t_{C2}$, $t_{D2}$) of respective pulse signals from respective counter circuits 46a to 46d, and the judging signal to distinguish the kind of the slit scanning direction by the sensor 16, then measures the time differences (the phase difference) of a pair of the photo-receiving elements which are placed in the meridian direction to be measured relative to the center thereof.

Once the time differences is obtained, it is converted into the terms of the refractive power. There is the relationships between the time difference which is measured by the phase difference method and the refractive power as shown in above-mentioned FIG. 8, therefore, for example, the value of the refractive power corresponding to the time difference is obtained by sampling the data by using the model eye of which the refractive-power is known in advance, and then by making the data be stored.

In addition, the three parameters S (spherical power), C (astigmatism (cylindrical) power), A (astigmatism (cylindrical) axial angle) as the same as the conventional art are obtained as following. If the value obtained based on the phase difference between a pair of the photo-receiving elements 15a and 15b, in the case that the slit light bundle is scanned by the slit aperture 90a, is defined as D1, and the value obtained based on the phase difference between another pair of the photo-receiving elements 15c and 15d is defined as D2, and as the same way, in the case that the slit light bundle is scanned by the slit aperture 90b, the value obtained based on the phase difference between a pair of the photo-receiving elements 15a and 15b is defined as D3, and the value obtained based on the phase difference between another pair of the photo-receiving elements 15c and 15d is defined as D4, then the following expressions are given:

$$D1 = S + C \cos^2\theta,$$

$$D2 = (C/2) \sin 2\theta,$$

$$D3 = -(C/2) \sin 2\theta,$$

$$D4 = S + C \sin^2\theta,$$

whereby respective values S, C and A (=θ) by processing arithmetically above-relationship equations.

The measurement result obtained as described above is displayed on the display part 51. At the same time, in the case that the there is the predetermined difference between the refractive power in the meridian direction to be measured with respect to the corneal center, it is displayed that the irregular astigmatism exists. The degree of difference thereof and the meridian direction to be measured may be displayed.

Figure 18:
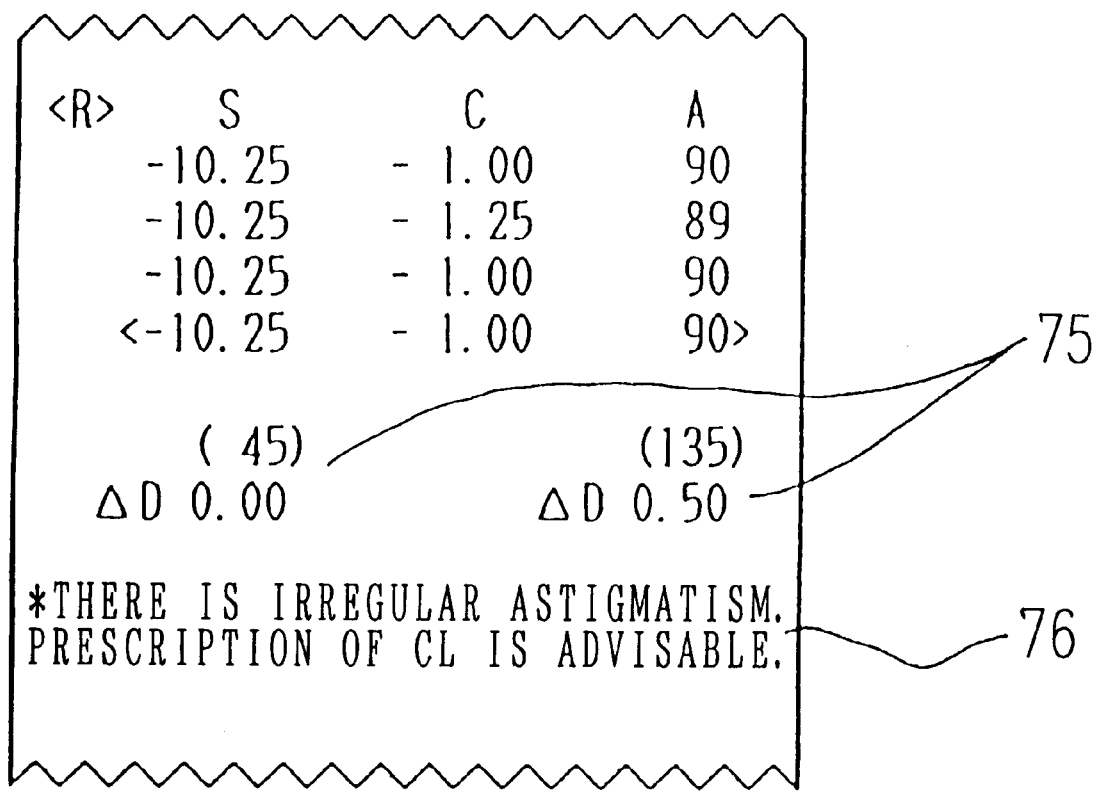
FIG. 18 is a view showing an example of printed out record performed by the apparatus of the second preferred embodiment.

Further, in the case that the measurement result is printed out by the printer 52, as shown in FIG. 18, difference 75 of the refractive power at the positions of respective photo-receiving elements with respect to the center every meridian directions to be measured (referring to this preferred embodiment, the directions of 45° and 135°) are displayed in addition to the values S, C and A. Also, if difference thereof is not less than the predetermined value (for example, ΔD>0.5 diopter), then such message display 76 that the irregular astigmatism exists and the prescription of contact lens is advisable is displayed. Such display reminds the examiner to confirm the values S, C and A obtained by the apparatus repeatedly and carefully in case of the visual inspection continued to following the final prescription.

Figure 19:
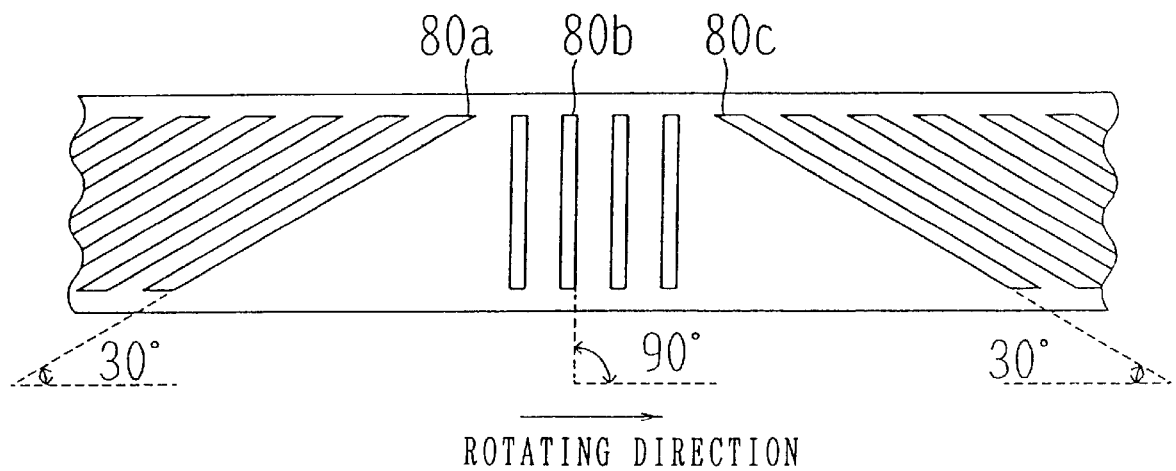
FIG. 19 is a view showing an example of an arrangement of slit apertures which are provided at the side face of the rotation sector in the case that the measurement of three meridian directions are performed, according to the modified example of the preferred embodiment.
Figure 20:
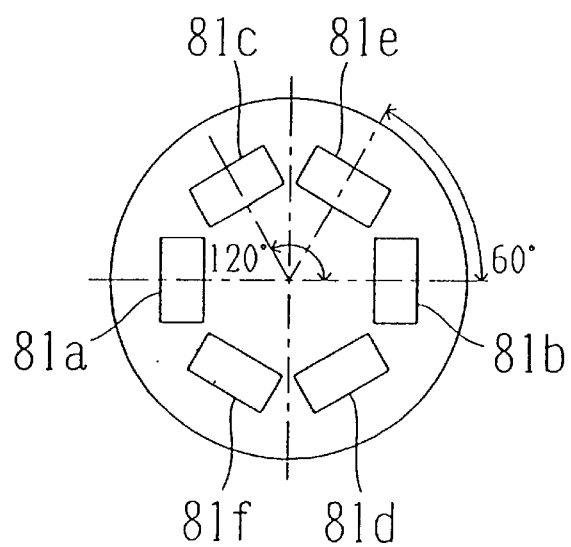
FIG. 20 is a view showing an example of an arrangement of photo-receiving elements in the case that the measurement of three meridian directions shown in FIG. 19 are performed.

Referring to the second preferred embodiment, the measurement in the two meridian directions by the two pairs of the photo-receiving elements is described, also the number of the scanning direction of the slit light bundle and the number of the arrangement of the photo-receiving elements may be increased in order to rise further the measurement accuracy. For example, in the case of the measurement of the three meridian directions, the rotation sector 4 is provided with the slit apertures 80a, 80b and 80c having three kinds of inclination angles of 30°, 90° and −30° relative to the rotation direction (see FIG. 19). On the contrary, a pair of the photo-receiving elements 81a and 81b, a pair of the photo-receiving elements 81c and 81d, and a pair of the photo-receiving elements 81e and 81f are provided at the intervals of angles of 60° respectively so as to be symmetric with respect to the optical axis in order to make correspond to the direction of the three kinds of the slit apertures for the photo-receiving section 14 (see FIG. 20). In this case, if the direction of the slit aperture (the scanning direction of the slit light bundle on the fundus of the eye E) corresponds to the direction of the photo-receiving elements 81a and 81b, the center of the scanning direction of the slit light bundle can be determined by using above-mentioned method based on the phase difference of a pair of the photo-receiving elements 81c and 81d or a pair of the photo-receiving elements 81e and 81f, whereby the refractive power of the respective parts of the cornea corresponding to respective photo-receiving elements of respective meridian directions with respect to the center can be measured.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic measurement apparatus for measuring a refractive power of an eye to be examined, the apparatus comprising:

slit projecting optical system for scanning a fundus of the eye by a slit light bundle;

detecting optical system for detecting the slit light bundle reflected by the fundus which is scanned by said slit projecting optical system, said detecting optical system includes plural pairs of photo-receiving elements which are disposed along a meridian direction corresponding to a slit scanning direction of the slit light bundle, and respective pairs of photo-receiving elements are disposed so as to be symmetric with putting an optical axis therebetween at an approximately conjugate position relative to a cornea of the eye;

rotating means for rotating synchronously the slit light bundle projected by said slit projecting optical system and the photo-receiving elements of said detecting optical system with the center at respective optical axes; and rotation controlling means for controlling to drive said rotating means at the predetermined angle intervals; and refractive power calculating means for calculating the refractive power at respective parts of the cornea corresponding to positions of respective photo-receiving elements at every numerous meridian directions in order to obtain overall distribution of the refractive power of the eye which is varied at the meridian direction, based on respective phase difference signals outputted by respective photo-receiving elements of said detecting optical system.

2. The ophthalmic measurement apparatus according to claim 1, further comprising:

displaying means for displaying the distribution of the refractive power obtained by said refractive power calculating means.

3. The ophthalmic measurement apparatus according to claim 2, wherein said displaying means includes means for displaying geometrically the distribution of the refractive power obtained by said refractive power calculating means.

4. The ophthalmic measurement apparatus according to claim 1, wherein said detecting optical system includes at least a pair of second photo-receiving elements which are disposed along a meridian direction not corresponding to the slit scanning direction of the slit light bundle, and respective pairs of second photo-receiving elements are disposed so as to be symmetric with putting the optical axis therebetween at approximately conjugate position relative to the cornea in order to detect the slit light bundle reflected by the fundus, and the apparatus further comprising:

center sensing means for sensing either a corneal center or a visual axis center based on a phase difference signal between at least a pair of said second photo-receiving elements, wherein said refractive power calculating means calculates the refractive power with reference to either the corneal center or the visual axis center based on respective phase difference signals between either the corneal center or the visual axis center sensed by said center sensing means and respective photo-receiving elements which are disposed along the meridian direction corresponding to the slit scanning direction of the slit light bundle.

5. The ophthalmic measurement apparatus according to claim 4, wherein said center sensing means senses either the corneal center or the visual axis center by obtaining the center position based on the time difference of the middle value between rise and decay of photo-voltage signals outputted respectively by at least a pair of said second photo-receiving elements which are disposed along the meridian direction not corresponding to the slit scanning direction of the slit light bundle.

6. The ophthalmic measurement apparatus according to claim 1, further comprising:

pupil diameter measurement means for measuring a pupil diameter of the eye based on signals outputted by photo-receiving elements of said detecting optical system.

7. The ophthalmic measurement apparatus according to claim 1, wherein said slit projecting optical system includes means for projecting slit light bundles having angles of inclination at least not less than two, and said detecting optical system includes plural pairs of photo-receiving elements which are disposed at meridian directions corresponding to slit scanning directions of the slit light bundles having respective angles of inclination so as to be symmetric with putting the optical axis therebetween.

8. The ophthalmic measurement apparatus according to claim 1, further comprising:

target projecting means for projecting the target for use in measuring corneal shape onto the cornea of the eye; and corneal shape measurement means for obtaining the shape of respective areas of the cornea by detecting and processing the target image which is formed by projecting the target onto the cornea by said target projecting means.

9. The ophthalmic measurement apparatus according to claim 8, wherein said target projecting means projects the target for use in measuring corneal shape which has plural circular patterns onto the cornea of the eye.

10. The ophthalmic measurement apparatus according to claim 8, further comprising:

measurement mode changing means for changing over between the corneal shape measurement mode for measuring the corneal shape by said corneal shape measurement means and the refractive power measurement mode for measuring the refractive power of the eye by said refractive power calculating means.

11. An ophthalmic measurement apparatus for measuring refractive power of an eye to be examined, the apparatus comprising:

slit projecting optical system for scanning a fundus of the eye by a slit light bundle;

detecting optical system for detecting the slit light bundle reflected by the fundus which is scanned by said slit projecting optical system by means of plural pairs of photo-receiving elements which are disposed so as to be symmetric with putting an optical axis therebetween at approximately conjugate position relative to a cornea of the eye, said plural pairs of photo-receiving elements includes at least a pair of first photo-receiving elements which are disposed along a meridian direction corresponding to a slit scanning direction of the slit light bundle and at least a pair of second photo-receiving elements which are disposed along a meridian direction not corresponding to the slit scanning direction of the slit light bundle;

center sensing means for sensing either a corneal center or a visual axis center based on a phase difference signal between at least a pair of said second photo-detecting elements; and refractive power calculating means for calculating the refractive power at respective parts of the cornea corresponding to positions of respective photo-receiving elements with reference to either the corneal center or the visual axis center based on respective phase difference signals between either the corneal center or the visual axis center sensed by said center sensing means and respective first photo-receiving elements which are disposed along the meridian direction corresponding to the slit scanning direction of the slit light bundle.

12. The ophthalmic measurement apparatus according to claim 11, wherein said center sensing means senses either the corneal center or the visual axis center by obtaining the center position based on the time difference of the middle value between rise and decay of photo-voltage signals outputted respectively by at least a pair of said second photo-receiving elements which are disposed along the meridian direction not corresponding to the slit scanning direction of the slit light bundle.

13. The ophthalmic measurement apparatus according to claim 11, further comprising:

judging means for judging the existence of irregular astigmatism based on the result calculated by said refractive power calculating means;

displaying means for displaying the result judged by said judging means; and recording means for recording the result judged by said judging means.

14. The ophthalmic measurement apparatus according to claim 11, further comprising:

refractive power difference calculating means for calculating the difference of refractive power of respective parts of the cornea based on the result calculated by said refractive power calculating means;

displaying means for displaying the result calculated by said refractive power difference calculating means; and recording means for recording the result calculated by said refractive power difference calculating means.

15. The ophthalmic measurement apparatus according to claim 11, wherein said slit projecting optical system projects at least two scanning directional slit light bundles, said first photo-receiving elements are disposed at a meridian direction corresponding to first scanning direction, and said second photo-receiving elements are disposed at a meridian direction corresponding to second scanning direction.

16. An ophthalmic measurement apparatus for measuring refractive power of an eye to be examined, the apparatus comprising:

slit projecting optical system for scanning a fundus of the eye by a slit light bundle;

detecting optical system for detecting the slit light bundle reflected by the fundus which is scanned by said slit projecting optical system, said detecting optical system includes plural photo-receiving elements which are disposed along a meridian direction corresponding to a slit scanning direction of the slit light bundle at approximately conjugate position relative to a cornea of the eye, and respective photo-receiving elements are disposed at positions to which distances from an optical axis are different;

rotating means for rotating synchronously the slit light bundle projected by said slit projecting optical system and the photo-receiving elements of said detecting optical system with the center at respective optical axes;

rotation controlling means for controlling to drive said rotating means at the predetermined angle intervals; and refractive power calculating means for calculating the refractive power at respective parts of the cornea corresponding to positions of respective photo-receiving elements at every numerous meridian directions in order to obtain overall distribution of the refractive power which is varied at the meridian direction, based on respective phase difference signals outputted by respective photo-receiving elements of said detecting optical system.

17. The ophthalmic measurement apparatus according to claim 16, further comprising:

displaying means for displaying the distribution of the refractive power obtained by said refractive power calculating means.

18. The ophthalmic measurement apparatus according to claim 16, wherein said detecting optical system includes at least a pair of second photo-receiving elements which are disposed along a meridian direction not corresponding to the slit scanning direction of the slit light bundle, and respective pairs of second photo-receiving elements are disposed so as to be symmetric with putting an optical axis therebetween at approximately conjugate position relative to the cornea of the eye in order to detect the slit light bundle reflected by the fundus of the eye, and the apparatus further comprising:

center sensing means for sensing either a corneal center or a visual axis center based on the phase difference signal between at least a pair of said second photo-receiving elements, wherein said refractive power calculating means calculates the refractive power based on respective phase difference signals between either the corneal center or the visual axis center sensed by said center sensing means and respective photo-receiving elements which are disposed along the meridian direction corresponding to the slit scanning direction of the slit light bundle.

19. The ophthalmic measurement apparatus according to claim 18, wherein said center sensing means senses either the corneal center or the visual axis center by obtaining the center position based on time difference of middle value between rise and decay of photo-voltage signals outputted respectively by at least a pair of said second photo-receiving elements which are disposed along the meridian direction not corresponding to the slit scanning direction of the slit light bundle.

* * * * *